United States Patent
Kural et al.

(10) Patent No.: US 10,204,207 B2
(45) Date of Patent: *Feb. 12, 2019

(54) SYSTEMS AND METHODS FOR TRANSCRIPTOME ANALYSIS

(71) Applicant: Seven Bridges Genomics Inc., Cambridge, MA (US)

(72) Inventors: Deniz Kural, Somerville, MA (US); Nathan Meyvis, Somerville, MA (US)

(73) Assignee: Seven Bridges Genomics Inc., Cambridge, MA (US)

( * ) Notice: Subject to any disclaimer, the term of this patent is extended or adjusted under 35 U.S.C. 154(b) by 751 days.

This patent is subject to a terminal disclaimer.

(21) Appl. No.: 14/744,536

(22) Filed: Jun. 19, 2015

(65) Prior Publication Data

US 2015/0302145 A1 Oct. 22, 2015

Related U.S. Application Data

(63) Continuation of application No. 14/157,759, filed on Jan. 17, 2014, now Pat. No. 9,063,914.

(60) Provisional application No. 61/893,467, filed on Oct. 21, 2013.

(51) Int. Cl.
*G06F 19/22* (2011.01)
*G06F 19/28* (2011.01)

(52) U.S. Cl.
CPC .............. *G06F 19/22* (2013.01); *G06F 19/28* (2013.01)

(58) Field of Classification Search
None
See application file for complete search history.

(56) References Cited

U.S. PATENT DOCUMENTS

| | | |
|---|---|---|
| 4,683,195 A | 7/1987 | Kary et al. |
| 4,683,202 A | 7/1987 | Mullis |
| 4,988,617 A | 1/1991 | Landegren et al. |
| 5,234,809 A | 8/1993 | Boom et al. |
| 5,242,794 A | 9/1993 | Whiteley et al. |
| 5,494,810 A | 2/1996 | Barany et al. |
| 5,511,158 A | 4/1996 | Sims |
| 6,054,278 A | 4/2000 | Dodge et al. |
| 6,223,128 B1 | 4/2001 | Allex et al. |
| 6,582,938 B1 | 6/2003 | Su et al. |
| 7,321,623 B2 | 1/2008 | Dambrackas |
| 7,483,585 B2 | 1/2009 | Brakus |
| 7,577,554 B2 | 8/2009 | Lystad et al. |
| 7,580,918 B2 | 8/2009 | Chang et al. |
| 7,776,616 B2 | 8/2010 | Heath et al. |
| 7,809,509 B2 | 10/2010 | Milosavljevic |
| 7,885,840 B2 | 2/2011 | Sadiq et al. |
| 7,957,913 B2 | 6/2011 | Chinitz et al. |
| 8,165,821 B2 | 4/2012 | Zhang |
| 8,209,130 B1 | 6/2012 | Kennedy et al. |
| 8,340,914 B2 | 12/2012 | Gatewood et al. |
| 8,639,847 B2 | 1/2014 | Blaszczak et al. |
| 8,972,201 B2 | 3/2015 | Mande et al. |
| 9,092,402 B2 | 7/2015 | Kural et al. |
| 9,116,866 B2 | 8/2015 | Kural |
| 9,390,226 B2 | 7/2016 | Kural |
| 9,617,944 B2 | 11/2017 | Kural |
| 2002/0190663 A1 | 12/2002 | Rasmussen |
| 2004/0023209 A1 | 2/2004 | Jonasson |
| 2005/0089906 A1 | 4/2005 | Furuta et al. |
| 2008/0003571 A1 | 1/2008 | McKernan et al. |
| 2008/0077607 A1 | 3/2008 | Gatawood et al. |
| 2008/0281463 A1 | 11/2008 | Suh et al. |
| 2009/0233809 A1 | 9/2009 | Faham et al. |
| 2009/0318310 A1 | 12/2009 | Liu et al. |
| 2009/0325145 A1 | 12/2009 | Sablon et al. |
| 2010/0041048 A1 | 2/2010 | Diehl et al. |
| 2010/0169026 A1 | 7/2010 | Sorenson et al. |
| 2010/0240046 A1 | 9/2010 | Palmer et al. |
| 2010/0285578 A1 | 11/2010 | Selden et al. |
| 2011/0004413 A1 | 1/2011 | Carnevali et al. |
| 2011/0096193 A1 | 4/2011 | Egawa |
| 2011/0098193 A1 | 4/2011 | Kingsmore et al. |
| 2011/0257889 A1 | 10/2011 | Klammer et al. |
| 2012/0157322 A1 | 6/2012 | Myllykangas et al. |
| 2012/0330566 A1 | 12/2012 | Chaisson |
| 2013/0059740 A1 | 3/2013 | Drmanac et al. |
| 2013/0073214 A1 | 3/2013 | Hyland et al. |
| 2013/0124573 A1 | 5/2013 | Seth et al. |
| 2013/0232480 A1 | 9/2013 | Winterfeldt et al. |
| 2013/0311106 A1 | 11/2013 | White et al. |
| 2013/0332081 A1 | 12/2013 | Reese et al. |
| 2013/0345066 A1 | 12/2013 | Brinza et al. |
| 2014/0012866 A1 | 1/2014 | Bowman et al. |
| 2014/0025312 A1 | 1/2014 | Chin et al. |
| 2014/0051588 A9 | 2/2014 | Drmanac et al. |

(Continued)

FOREIGN PATENT DOCUMENTS

| KR | 101282798 B1 | 7/2013 |
|---|---|---|
| TW | 201243117 A | 11/2012 |

(Continued)

OTHER PUBLICATIONS

LeGault et al. (Learning Probabilistic Splice Graphs from RNA-Seq data; Dec. 20, 2010; pp. 1-8 ).*

(Continued)

*Primary Examiner* — Lori A. Clow
(74) *Attorney, Agent, or Firm* — Kip L. Bodi

(57) ABSTRACT

The invention generally provides systems and methods for analysis of RNA-Seq reads in which an annotated reference is represented as a directed acyclic graph (DAG) or similar data structure. Features such as exons and introns from the reference provide nodes in the DAG and those features are linked as pairs in their canonical genomic order by edges. The DAG can scale to any size and can in fact be populated in the first instance by import from an extrinsic annotated reference.

20 Claims, 7 Drawing Sheets

Specification includes a Sequence Listing.

(56) References Cited

U.S. PATENT DOCUMENTS

| | | |
|---|---|---|
| 2014/0129201 A1 | 5/2014 | Kennedy et al. |
| 2014/0136120 A1 | 5/2014 | Colwell et al. |
| 2014/0200147 A1 | 7/2014 | Bartha et al. |
| 2014/0278590 A1 | 9/2014 | Abbassi et al. |
| 2014/0280360 A1 | 9/2014 | Webber et al. |
| 2014/0281708 A1 | 9/2014 | Adam et al. |
| 2014/0323320 A1 | 10/2014 | Jia et al. |
| 2015/0020061 A1 | 1/2015 | Ravi |
| 2015/0056613 A1 | 2/2015 | Kural |
| 2015/0057946 A1 | 2/2015 | Kural |
| 2015/0066383 A1 | 3/2015 | Wernicke |
| 2015/0110754 A1 | 4/2015 | Bai et al. |
| 2015/0112602 A1 | 4/2015 | Kural et al. |
| 2015/0112658 A1 | 4/2015 | Kural et al. |
| 2015/0197815 A1 | 7/2015 | Kural |
| 2015/0199472 A1 | 7/2015 | Kural |
| 2015/0199473 A1 | 7/2015 | Kural |
| 2015/0199474 A1 | 7/2015 | Kural |
| 2015/0199475 A1 | 7/2015 | Kural |
| 2015/0227685 A1 | 8/2015 | Kural |
| 2015/0293994 A1 | 10/2015 | Kelly |
| 2015/0302145 A1 | 10/2015 | Kural et al. |
| 2015/0310167 A1 | 10/2015 | Kural et al. |
| 2015/0344970 A1 | 12/2015 | Vogelstein et al. |
| 2015/0347678 A1 | 12/2015 | Kural |
| 2015/0356147 A1 | 12/2015 | Mishra et al. |
| 2016/0259880 A1 | 9/2016 | Semenyuk |
| 2016/0306921 A1 | 10/2016 | Kural |
| 2016/0364523 A1 | 12/2016 | Locke et al. |
| 2017/0058320 A1 | 3/2017 | Locke et al. |
| 2017/0058341 A1 | 3/2017 | Locke et al. |
| 2017/0058365 A1 | 3/2017 | Locke et al. |
| 2017/0198351 A1 | 7/2017 | Lee et al. |
| 2017/0199959 A1 | 7/2017 | Locke |
| 2017/0199960 A1 | 7/2017 | Ghose et al. |
| 2017/0242958 A1 | 8/2017 | Brown |

FOREIGN PATENT DOCUMENTS

| | | |
|---|---|---|
| WO | 2010010992 A1 | 1/2010 |
| WO | 2011139797 A2 | 11/2011 |
| WO | 2012096579 A3 | 7/2012 |
| WO | 2012098515 A1 | 7/2012 |
| WO | 2012142531 A2 | 10/2012 |
| WO | 2013035904 A1 | 3/2013 |
| WO | 2013043909 A1 | 3/2013 |
| WO | 2013097257 A1 | 7/2013 |
| WO | 2013106737 A1 | 7/2013 |
| WO | 2013184643 A1 | 12/2013 |
| WO | 2015027050 A1 | 2/2015 |
| WO | 2015048753 A1 | 4/2015 |
| WO | 2015058093 A1 | 4/2015 |
| WO | 2015058095 A1 | 4/2015 |
| WO | 2015058097 A1 | 4/2015 |
| WO | 2015058120 A1 | 4/2015 |
| WO | 2015061099 A1 | 4/2015 |
| WO | 2015061103 A1 | 4/2015 |
| WO | 2015105963 A1 | 7/2015 |
| WO | 2015123269 A1 | 8/2015 |
| WO | 2016141294 A1 | 9/2016 |
| WO | 2016201215 A1 | 12/2016 |
| WO | 2017120128 A1 | 7/2017 |
| WO | 2017123864 A1 | 7/2017 |
| WO | 2017147124 A1 | 8/2017 |

OTHER PUBLICATIONS

Garber et al. (Nature Methods Jun. 2011, vol. 8, No. 6:469-478).*
Trapnell et al. (Nature Biotechnology (2010) vol. 28:511-515).*
Guttman et al. (Nature Biotechnology (2010) vol. 28:503-510).*
Abouelhoda, 2012, Tavaxy: integrating Taverna and Galaxy workflows with cloud computing support, BMC BioinforMatics 13:77.
Agarwal, 2013, SINNET: Social Interaction Network Extractor from Text, Proc IJCNLP 33-36.
Aguiar, 2012, HapCompass: A fast cycle basis algorithm for accurate haplotype assembly of sequence data, J Comp Biol 19(6):577-590.
Aguiar, 2013, Haplotype assembly in polyploid genomes and identical by descent shared tracts, BioInformatics 29(13):i352-i360.
Airoldi, 2008, Mixed membership stochastic blockmodels, JMLR 9:1981-2014.
Albers et al., Dindel: Accurate indel calls from short-read data, 2011, pp. 961-973, vol. 21, Genome Research.
Albers, 2011, Dindel: Accurate indel calls from short-read data, Genome Research 21:961-973.
Bansal, 2008, An MCMC algorithm for haplotype assembly from whole-genome sequence data, Genome Res 18:1336-1346.
Bao, 2013, BRANCH: boosting RNA-Seq assemblies with partial or related genomic sequences, Bioninformatics 29(10):1250-1259.
Bertrand, 2009, Genetic map refinement using a comparative genomic approach, J Comp Biol 16(10):1475-1486.
Boyer, 1977, A Fast String Searching Algorithm, Comm ACM 20(10):762-772.
Brose et al., Cancer Risk Estimates for BRCA1 Mutation Carriers Identified in a Risk Evaluation Program, 2002, pp. 1365-1372, vol. 94, Journal of the National Cancer Institute.
Buhler, 2001, Search algorithms for biosequences using random projection, dissertation, University of Washington (203 pages); retreived from the internet on Jun. 3, 2016, at https://pdfs.semanticscholar.org.
Chen, 2012, Transient hypermutability, chromothripsis and replication-based mechanisms in the generation of concurrent clustered mutations, Mutation Res 750(1):562-59.
Chen, 2014, Genome architecture and its role in human copy number variation, Genomics Inform 12(4):1 36-144.
Chuang, 2001, Gene recognition based on DAG shortest paths, Bioinformatics 17(Suppl. 1):s56-s64.
Clark, 2014, Illumina announces landmark $1,000 human genome sequencing, Wired, Jan. 15, 2014.
Cock, 2013, Galaxy tools and workflows for sequence analysis with applications in molecular plant pathology, Peer J 1:e167, pp. 1-22.
Cohen-Boulakia, 2014, Distilling structure in Taverna scientific workflows: a refactoring approach, BMC Bioinformatics 15(Suppl 1):S12.
DePristo, 2011, A framework for variation discovery and genotyping using next-generation DNA sequencing data, Nat Gen 43:491-498.
Dinov, 2011, Applications of the pipeline environment for visual informatics and genomic computations, BMC Bioinformatics 12:304.
Duan et al., Optimizing de novo common wheat transcriptome assembly using short-read RNA-Seq data. (2012) pp. 1-12, vol. 13, BMC Genomics.
Durbin, 2014, Efficient haplotype matching and storage using the positional Burrows-Wheeler transform (PBWT), Bioinformatics 30(9):1266-1272.
Fiers, 2008, High-throughput Bioinformatics with the Cyrille2 Pipeline System, BMC Bioinformatics 9:96.
Flicek, 2009, Sense from sequence reads: methods for alignment and assembly, Nat Meth Suppl 6(11s):s6-s12.
Florea, 2013, Genome-guided transcriptome assembly in the age of next-generation sequencing, IEEE/ACM Trans Comp Biol Bioinf 10(5):1234-1240.
Friedman, The World is Flat, 2005, pp. 94-95, Farrar, Straus, and Giroux, New York.
Glusman, 2014, Whole-genome haplotyping approaches and genomic medicine, Genome Med 6:73.
Gotoh, 1999, Multiple sequence alignment: algorithms and applications, Adv Biophys 36:159-206.
Grasso, 2004, Combining partial order alignment and progressive multiple sequence alignment increases alignment speed and scalability to very large alignment problems, Bioinformatics 20(10):1546-1556.
Harenberg, 2014, Community detection in large-scale networks: a survey and empirical evaluation, WIREs Comp Stat 6:426-439.
He, 2010, Optimal algorithms for haplotype assembly from whole-genome sequence data, Bioinformatics 26:i183-i190.

(56) References Cited

OTHER PUBLICATIONS

Hokamp, 2003, Wrapping up BLAST and Other Applications for Use on Unix Clusters, Bioinformatics 19(3)441-42.
Homer, 2010, Improved variant discovery through local re-alignment of short-read next generation sequencing data using SRMA, Genome Biol 11(10):R99.
Horspool, 1980, Practical Fast Searching in Strings, Software—Practice & Experience 10:501-506.
Hull, 2006, Taverna: a tool for building and running workflows of services, Nucl Acids Res 34(Web Server issue):W729-32.
Hutchinson, 2014, Allele-specific methylation occurs at genetic variants associated with complex diseases, PLoS One 9(6):e98464.
International Search Report and Written Opinion dated Mar. 31, 2015 for International Application No. PCT/US2015/010604 filed Jan. 8, 2015 (13 pages).
International Search Report and Written Opinion dated Dec. 30, 2014, for PCT/US14/58328, with International Filing Date Sep. 30, 2014 (15 pages).
International Search Report and Written Opinion dated Feb. 17, 2015, for International Patent Application No. PCT/US2014/061156, filed Oct. 17, 2014 (19 pages).
International Search Report and Written Opinion dated Jan. 10, 2017, for application No. PCT/US16/57324 with international filing date Oct. 17, 2016 (7 pages).
International Search Report and Written Opinion dated Jan. 5, 2016, for International Patent Application PCT/US2015/054461 with International Filing Date Oct. 7, 2015 (7 pages).
International Search Report and Written Opinion dated Mar. 19, 2015, for International Application No. PCT/US2014/061162 with International Filing Date Oct. 17, 2014 (12 pages).
International Search Report and Written Opinion dated May 11, 2015, for International Patent Application No. PCT/US2015/015375 with International Filing Date Feb. 11, 2015 (12 pages).
International Search Report and Written Opinion dated May 5, 2016, for International Patent Application No. PCT/US2016/020899 wiht International Filing Date Mar. 4, 2016 (12 pages).
International Search Report and Written Opinion dated Apr. 7, 2017, for International Patent Application No. PCT/US17/13329, filed Jan. 13, 2017 (9 pages).
International Search Report and Written Opinion dated Dec. 30, 2014, for International Patent Application No. PCT/US14/58328, filed Sep. 30, 2014 (22 pages).
International Search Report and Written Opinion dated Feb. 4, 2015, for International Patent Application No. PCT/US2014/061198, filed Oct. 17, 2014 (8 pages).
International Search Report and Written Opinion dated Feb. 10, 2015, for International Patent Application No. PCT/US2014/060690, filed Oct. 15, 2014 (11 pages).
International Search Report and Written Opinion dated Feb. 4, 2015, for Patent Application No. PCT/US2014/061158, filed Oct. 17, 2014, (11 pages).
International Search Report and Written Opinion dated Sep. 2, 2016, for International Patent Application No. PCT/US2016/033201 with International Filing Date May 19, 2016 (14 pages).
International Search Report and Written Opinion dated Sep. 7, 2016, for International Application No. PCT/US2016/036873 with International filing date Jun. 10, 2016 (8 pages).
International Search Report and Written Opinion of the International Searching Authority dated Nov. 17, 2015 for International Application No. PCT/US2015/048891 (11 Pages).
Kano, 2010, Text mining meets workflow: linking U-Compare with Taverna, Bioinformatics 26(19):2486-7.
Katoh, 2005, MAFFT version 5: Improvement in accuracy of multiple sequence alignment, Nucl Acids Res 33(2):511-518.
Kim, 2008, A Scaffold Analysis Tool Using Mate-Pair Information in Genome Sequencing, Journal of Biomedicine and Biotechnology 8(3):195-197.
Koolen, 2008, Clinical and Molecular Delineation of the 17q21.31 Microdeletion Syndrome, J Med Gen 45(11):710-720.
Krabbenhoft, 2008, Integrating ARC grid middieware with Taverna workflows, Bioinformatics 24(9):1221-2.
Lanzen, 2008, The Taverna Interaction Service: enabling manual interaction in workflows, Bioinformatics 24(8):1118-20.
Layer, 2015, Efficient genotype compression and analysis of large genetic-variation data sets, Nat Meth 13(1):63-65.
Lee et al. Accurate read mapping using a graph-based human pan-genome. (May 2015) American Society of Human Genetics 64th Annual Meeting Platform Abstracts; Abstract 41.
Lee, 2014, Accurate read mapping using a graph-based human pan-genome, ASHG 2014 Abstracts.
Lee, 2014, MOSAIK: A hash-based algorithm for accurate next-generation sequencing short-read mapping, PLoS One 9(3):e90581.
Li, 2008, Automated manipulation of systems biology models using IIbSBML within Taverna workflows, Bioinformatics 24(2):287-9.
Li, 2008, Performing statistical analyses on quantitative data in Taverna workflows: an example using R and maxdBrowse to identify differentially-expressed genes from microarray data, BMC Bioinforrnatics 9:334.
Li, 2009, Fast and accurate short read alignment with Burrows-Wheeler Transform. Bioinformatics 25:1754-60.
Life Technologies, 2013, Rapid Exome Sequencing Using the Ion Proton System and Ion Ampliseq Technology, Application Note (5 Pages).
Machine translation of KR 10-1282798 B1 generated on Jan. 6, 2016, by the website of the European Patent Office (23 pages).
Machine translation produced on Jun. 1, 2015, by Espacenet of WO 2010/010992 A1 (11 pages).
Machine translation produced on Jun. 1, 2015, by WPIO website of WO 2013/035904 (10 pages).
Mamoulis, 2004, Non-contiguous sequence pattern queries, in Advances in Database Technology—EDBT 2004: 9th International Conference on Extending Database Technology, Heraklion, Crete, Greece, Mar. 14-18, 2004, Proceedings (18 pages); retrieved from the internet on Jun. 3, 2016, at https://link.springer.com/content/pdf/10.1007%2Fb95855.pdf.
Marth et al., A general approach to single-nucleotide polymorphism discovery, Dec. 1999, pp. 452-456, vol. 23, Nature Genetics.
Marth, 1999, A general approach to single-nucleotide polymorphism discovery, Nature Genetics 23:452-456.
Mazrouee, 2014; FastHap: fast and accurate single individual haplotype reconstructions using fuzzy conflict graphs, Bioinformatics 30:i371-i378.
McKenna, 2010, The Genome Analysis Toolkit: a MapReduce framework for analyzing next-generation DNA sequencing data, Genome Res 20(9):1297-1303.
McSherry, 2001, Spectral partitioning of random graphs, Proc 42nd IEEE Symp Found Comp Sci 529-537.
Misra, 2011, Anatomy of a hash-based long read sequence mapping algorithm for next generation DNA sequencing, Bioinformatics 27(2):189-195.
Moudrianakis, 1965, Base sequence determination in nucleic acids with electron microscope III: chemistry and microscopy of guanine-labelled DNA, PNAS 53:564-71.
Newman et al. An ultrasensitive method for quantitating circulating tumor DNA with broad patient coverage. Apr. 2014, pp. 1-22, vol. 20, No. 5. Nature Medicine.
Ning, 2001, SSAHA: a fast search method for large DNA databases, Genome Res 11(10):1725-9.
Olnn, 2004, Taverna: a tool for the composition and enactment of bioinformatics workflows, Bioinformatics 20(17):3045-54.
Olnn, 2006, Taverna: lessons in creating a workflow environment for the life sciences, Concurrency and Computation: Practice and Experience 18(10):1067-1100.
Olsson et al. Serial monitoring of circulating tumor DNA in patients with primary breast cancer for detection of occult metastatic disease. May 2015, pp. 1034-1047, vol. 7, No. 8, EMBO Molecular Medicine.
Pop et al., 2004, Comparative genome assembly, Briefings in Bioinformatics vol. 5, pp. 237-248.
Posada, 1998, Model Test: testing the model of DNA substitution, Bioinformatics 14(9):817-8.

(56) References Cited

OTHER PUBLICATIONS

Potter, 2004, The ensemble analysis pipeline, Genome Res 14:934-941.
Ramirez-Gonzalez, 2011, Gee Fu: a sequence version and web-services database tool for genomic assembly, genome feature and NGS data, Bioinformatics 27(19):2754-2755.
Ronquist, 2012, MrBayes 3.2: efficient Bayesian phylogenetic inference and model choice across a large model space, Syst Biol 61(3):539-42.
Schenk, 2013, A pipeline for comprehensive and automated processing of electron diffraction data in IPLT, J Struct Biol 182(2):173-185.
Sroka, 2006, XQTav: an XQuery processor for Taverna environment, Bioinformatics 22(10):1280-1.
Sroka, 2010, A formal semantics for the Taverna 2 workflow model, J Comp Sys Sci 76(6):490-508.
Sroka, 2011, CalcTav—integration of a spreadsheet and Taverna workbench, Bioinformatics 27(18):2618-9.
Subramanian, 2008, DIALIGN-TX: greedy and progessive approaches for segment-based multiple sequence alignment, Alg Mol Biol 3(1):1-11.
Sudmant, 2015, An integrated map of structural variation in 2,504 human genomes, Nature 526:75-81.
Sun, 2006, Pairwise Comparison Between Genomic Sequences and Optical maps, dissertation, New York University (131 pages); retreived from the internet on Jun. 3, 2016, at https://pdfs.semanticscholar.org.
Tan, 2010, A Comparison of Using Taverna and BPEL in Building Scientific Workflows: the case of caGrid, Concurr Comput 22(9):1098-1117.
Tarhio, 1993, Approximate Boyer-Moore String Matching, SIAM J Comput 22(2):243-260.
Tewhey, 2011, The importance of phase information for human genomics, Nat Rev Gen 12:215-223.
The 1000 Genomes Project, 2015, A global reference for human genetic variation, Nature 526:68-74.
Thomas, 2014, Community-wide effort aims to better represent variation in human reference genome, Genome Web (11 pages).
Torri, 2012, Next generation sequence analysis and computational genomics using graphical pipeline workflows, Genes (Basel) 3(3):545-575.
Trapnell, 2009, TopHat: discovering splice junctions with RNA-Seq, Bioinformatics 25:1105-1111.
Turi, 2007, Taverna Workflows: Syntax and Semantics, IEEE Int Conf on e-Science and Grid Computing 441-448.
Wallace, 2005, Multiple sequence alignments, Curr Op Struct Biol 15(3):261-266.
Wheeler et al., The complete genome of an individual by massively parallel DNA sequencing, 2008, pp. 872-876, Nature.
Wolstencroft, 2005, Panoply of Utilities in Taverna, Proc 2005 1st Int Conf e-Science and Grid Computing 156-162.
Wolstencroft, 2013, The Taverna Workflow Suite: Designing and Executing Workflows of Web Services on the Desktop, Web or in the Cloud, Nucl Acids Res 41(W1):W556-W561.
Yang, 2013, Leveraging reads that span multiple single nucleotide polymorphisms for haplotype inference from sequencing data, Bioinformatics 29(18):2245-2252.
Zhang et al., Construction of a high-density genetic map for sesame based on large scale marker development by specific length amplified fragment (SLAF) sequencing. (2013) pp. 1-12, vol. 13, BMC Plant Biology.
Zhang, 2013, Taverna Mobile: Taverna workflows on Android, EMBnet J 19(B):43-45.
Barbieri, 2013, Exome sequencing identifies recurrent SPOP, FOXA1 and MED12 mutations in prostate cancer, Nature Genetics 44:6 685-689.
Beerenwinkel, 2007, Conjunctive Bayesian Networks, Bernoulli 13(4), 893-909.
Browning et al, Haplotype phasing: existing methods and new developments, 2011, vol. 12, Nature Reviews Genetics, 26 pages.
Caboche et al, Comparison of mapping algorithms used in high-throughput sequencing: application to Ion Torrent data, 2014, vol. 15, BMC Genomics, 16 pages.
Cartwright, DNA assembly with gaps (DAWG): simulating sequence evolution, 2005, pp. iii31-iii38, vol. 21, Oxford University Press.
Examination Report issued in SG 11201601124Y, 5 pages; dated Jan. 3, 2018.
Gerlinger, 2012, Intratumor Heterogeneity and Branched Evolution Revealed by Multiregion Sequencing, 366:10 883-892.
International Search Report and Written Opinion dated Aug. 31, 2017, for International Application No. PCT/US2017/018830 with International Filing Date Feb. 22, 20117, (11 pages).
Lecca, 2015, Defining order and timing of mutations during cancer progression: the TO-DAG probabilistic graphical model, Frontiers in Genetics, vol. 6 Article 309 1-17.
Mourad, 2012, A hierarchical Bayesian network approach for linkage disequilibrium modeling and data-dimensionality reduction prior to genome-wide association studies, BMC Bioinformatics 12:16 1-20.
Myers, The Fragment Assembly String Graph, Bioinformatics, 2005, pp. ii79-ii85, vol. 21.
Pruesse, 2012, SINA: Accurate high-throughput multiple sequence alignment of ribosomal RNA genes, Bioinformatics 28:14 1823-1829.
Sturgeon, RCDA: a highly sensitive and specific alternatively spliced transcript assembly tool featuring upstream consecutive exon structures, Genomics, Dec. 2012, 100(6): 357-362.
Uchiyama et al., CGAT: a comparative genome analysis tool for visualizing alignments in the analysis of complex evolutionary changes between closely related genomes, 2006, e-pp. 1-17, vol. 7:472; BMC Bioinformatics.
Vivian et al., Rapid and efficient analysis of 20,000 RNA-seq samples with Toil, bioRxiv, 2016, 85 pages.
Written Opinion issued in SG 11201603044S, 7 pages; dated Jul. 10, 2017.
Zeng, 2013, PyroHMMvar: a sensitive and accurate method to call short indels and SNPs for Ion Torrent and 454 data, Bioinformatics 29:22 2859-2868.

* cited by examiner

TTGGATATGGG (SEQ ID NO: 1)
TTGGATCGAATTATGGG (SEQ ID NO: 2)

FIG. 2

(SEQ ID NO: 6)　　　　　　　TGGATAGATGAA
(SEQ ID NO: 4)  AUGCAUUUCCGUGGAUAG<u>AUGAAA</u>AUGCAUCAGAAAUAG (SEQ ID NO: 6)　　　　　　　TGGATAGATGAA
(SEQ ID NO: 5)  AUGCAUUUCCGUGGAUAGAUGCAUCAGAAAUAG (SEQ ID NO: 6)　　　　　　　TGGATAGATGAA
(SEQ ID NO: 5) AUGCAUUUCCGUGGAUAGAUGCAUCAGAAAUAG

FIG. 4

TGGATAGATGAA (SEQ ID NO: 6)
AUGCAUUUCCGUGGAUAGAUGAAAAUGCAUCAGAAAUAG (SEQ ID NO: 4)
AUGCAUUUCCGUGGAUAGAUGCAUCAGAAAUAG (SEQ ID NO: 5)

Figure 3 from Nakao, et al., 2005, Large-scale analysis of human alternative protein isoforms: pattern classification and correlation with subcellular localization signals, Nucl Acids Res 33(8):2355-2363

SYSTEMS AND METHODS FOR TRANSCRIPTOME ANALYSIS

CROSS-REFERENCE TO RELATED APPLICATION

This application is a continuation of U.S. patent application Ser. No. 14/157,759, filed Jan. 17, 2014, now issued as U.S. Pat. No. 9,063,914, which application claims the benefit of, and priority to, U.S. Provisional Patent Application Ser. No. 61/893,467, filed Oct. 21, 2013, the contents of each of which are incorporated by reference.

SEQUENCE LISTING

This application contains a sequence listing which has been submitted in ASCII format via EFS-Web and is hereby incorporated by reference in its entirety. The ASCII-formatted sequence listing, created on Jun. 19, 2015, is named SBG-009-02US-1-Sequence_ST25, and is 1,177 bytes in size.

FIELD OF THE INVENTION

The invention generally relates to bioinformatics and particularly to analyses using directed acyclic data structures.

BACKGROUND

The transcriptome is the complete set of transcripts in a cell, and their quantity, for a specific developmental stage or physiological condition. The transcriptome is central to organismal function, development, and disease. The very nature and vitality of an organism arises from all of the transcripts (including mRNAs, non-coding RNAs and small RNAs), their expression levels, gene splicing patterns, and post-transcriptional modifications. In fact, a much greater fraction of the human genome than was expected is now known to be transcribed. See Bertone, et al., 2004, Global identification of human transcribed sequences with genome tiling arrays, Science 306:2242-2246.

Methods for transcriptome analysis based on next-generation sequencing (NGS) technologies have been reported. See, e.g., Wang, et al., 2009, RNA-Seq: a revolutionary tool for transcriptomics, Nat Rev Genet 10(1):57-63 2009. The RNA-Seq (RNA sequencing) method promises to rapidly generate high volumes of transcriptome data.

However, RNA-Seq faces informatics challenges, such as storing and analyzing large amounts of data, which must be overcome to make good use of the reads. The accepted approach to analyzing RNA-Seq reads involves mapping the short reads from RNA-Seq to a reference genome, or to assemble them into contigs before aligning using such programs as ELAND, SOAP31, MAQ32 and RMAP 33. Unfortunately, short transcriptomic reads present challenges not suited to analysis of, for example, reads that span exon junctions or that contain poly(A) tails. Additionally, with larger transcriptomes, many RNA-Seq reads will match multiple locations in the genome. Further, reads with multiple base mis-matches relative to a reference are difficult to align. Aligning and analyzing RNA-Seq reads presents problems not only in the nature of the information involved but also in the volume.

Some methods for read mapping, transcriptome reconstruction (i.e., identifying expressed genes and isoforms), as well as expression quantification (analysis of differential expression across samples) have been reported. See Garber, et al., 2011, Computational methods for transcriptome annotation and quantification using RNA-Seq, Nat Meth 8(6): 469-477. However, due to the nature and volume of RNA-Seq data generation, existing methods may prove inadequate in many cases. Read mapping with large data sets is computationally challenging and analytical methods for differential expression are only beginning to emerge. The computational demands of mapping the large number of reads from RNA-Seq are greatly multiplied by the large amount of reference data that are coming available.

For example, the GENCODE Consortium seeks to identify all gene features in the human genome that have been reported. Harrow, et al., 2012, GENCODE: The reference human genome annotation for The ENCODE Project, Genome Res 22:1760-1774. The volume of material encompassed by the GENCODE project is formidable. Not only do new protein-coding loci continue to be added, the number of alternative splicing transcripts annotated steadily increases. The GENCODE 7 release includes more than 20,000 protein-coding and almost 10,000 long noncoding RNA loci (lncRNA), as well as more than 33,000 coding transcripts not represented in other sources. GENCODE also includes other features such as untranslated regions (UTRs), long intergenic noncoding RNA (lincRNA) genes, short noncoding RNAs, and alternative splice patterns. Even with a resource like GENCODE, methods like RNA-Seq are revealing that differential transcript expression by cell type, tissue type, and development stage has yet to be fully understood, and also that there are many features such as novel exons yet to be documented in the human genome.

SUMMARY

The invention generally provides systems and methods for analysis of RNA-Seq reads in which an annotated reference is represented as a directed acyclic graph (DAG) or similar data structure. Features from the reference, such as exons and introns, provide nodes in the DAG and those features are linked to one another in their canonical genomic order by edges. The DAG can scale to any size and can, in fact, be populated in the first instance by imported sequence from an extrinsic annotated reference. Since alignment with a DAG is very rapid, particularly using methods herein, very large sets of RNA-Seq data can be analyzed against very large reference sets. Thus, using RNA-Seq to discover all isoforms of a transcriptome is not computationally intractable and transcriptomics can move at a pace and throughput not previously possible. One or any number of transcriptomes can be studied from one or any number of organisms to increase understanding of organismal function, development, and disease.

Aspects of the invention relate to creation of a maximal DAG that includes all or substantially all known features (e.g., exons, introns, etc.) of a reference. This maximal DAG data structure has applications in transcriptomics including, for example, identifying isoforms. Other aspects of the invention discussed herein relate to the creation of a DAG that includes at least some of the features of a reference, and use of that DAG in analyses. In a maximal DAG, no pair of nodes is not directly connected by an edge.

In certain aspects, the invention provides a method of identifying an isoform. The method includes representing—using a computer system comprising a processor coupled to a non-transitory memory—features from a genome as nodes and creating, for pairs of the features, edges connecting the members of the pair by their proximal ends. The nodes and edges are stored as a directed acyclic data structure in the computer memory and the method includes aligning a transcript sequence to a path comprising a subset of the features connected by a subset of the edges, thereby identifying an isoform corresponding to the path. Preferably, each of substantially all of the exons from the genome are included in the features and represented as nodes. In some embodiments, the plurality of features comprises all of the exons of a gene.

The method may include obtaining the features from an annotated transcriptome database such as GENCODE.

In some embodiments, the nodes and edges in the directed acyclic data structure represent both known and novel isoforms. Where an identified isoform is novel, aligning the transcript sequence can involve creating a new node or edge in the directed acyclic data structure. A new node can also be created for splice variants, e.g., where a one of the plurality of features and a second one of the plurality of features represent alternative versions of an exon differing by one codon.

The maximal DAG can be built—all or partly—prior to and independent of analyzing RNA-Seq reads. Thus, the method may include creating the edge for each pair of the plurality of features prior to aligning the transcript. For reasons related to the nature of directed acyclic data structures, the reference represented in the data structure can be arbitrarily large—e.g., hundreds or thousands of exons and introns.

In related aspects, the invention provides a system for identifying an isoform that includes a computer system comprising a processor coupled to a non-transitory memory. The computer system stores a directed acyclic data structure representing features from a genome as nodes and edges for pairs of the plurality of features, the edge connecting the two members of that pair by their proximal ends. Preferably, the features include substantially all or all exons and introns of the genome. The computer system is operable to align a transcript sequence to a path comprising a subset of the features connected by a subset of the edges, thereby identifying an isoform corresponding to the path.

In some embodiments, the computer system is operable to align a transcript sequence to a path comprising a subset of the features connected by a subset of the edges, thereby identifying an isoform corresponding to the path. The directed acyclic data structure may be created and stored therein prior to aligning the transcript. Preferably, the directed acyclic data structure represents substantially all exons from the genome. In certain embodiments, the plurality of features includes all of the exons of a gene. The system may be operable to obtain, from an annotated transcriptome database, information about the plurality of features to be represented. In some embodiments, the nodes and edges in the directed acyclic data structure represent some known isoforms and some novel isoforms. In certain embodiments, a first one of the plurality of features and a second one of the plurality of features represent alternative versions of an exon differing by one codon. One of the plurality of features may exist within a second one of the plurality of features on the genome. The plurality of features may comprise at least 100 exons.

Other aspects of the invention relate to aligning sequence reads to a directed acyclic data structure that substantially comprehensively represents an annotated reference. Using alignment algorithms of the invention, reads can be rapidly mapped despite the large numbers associated with RNA-Seq results and substantially comprehensive references.

In certain aspects, the invention provides methods of analyzing a transcriptome by obtaining a plurality of sequence reads from a transcriptome, finding alignments— each with an alignment score that meets a predetermined criteria—between the plurality of sequence reads and a directed acyclic data structure comprising nodes representing RNA sequences and edges connecting pairs of nodes, and identifying transcripts in the transcriptome based on paths through a directed acyclic data structure that include the alignments. The method is suited for analysis of reads obtained by RNA-Seq. The predetermined criteria may be, for example, the highest-scoring alignment.

The invention includes methods and systems for transcriptome analysis in which a DAG is used for a reference, which DAG need not be a maximal DAG. The invention exploits situations in which there is a priori data for the relative frequency of isoform counts. An isoform count distribution can be used to aid in mapping reads to a DAG by using that information to inform judgments about the likelihood that candidate alignments correspond to actual nucleotide sequences. In general, isoform counts provide an expected number of edge traversals when mapping reads from a transcriptome to a DAG. If an observed number deviates too greatly from the expected number, an alignment algorithm can be modified to punish (or favor) the traversal of unused edges and the alignment repeated. This can be done iteratively until the observed and expected usages are within some threshold difference of one another, causing reads being mapped to the DAG to yield a distribution that approaches the a priori distribution.

In some embodiments, the directed acyclic data structure represents substantially all known exons for at least one chromosome. The directed acyclic data structure may be created and stored prior to the finding the alignments. In some embodiments, the alignments are found by comparing each sequence read to at least a majority of the possible paths through the directed acyclic data structure. The method may include assembling the plurality of sequence reads into a contig based on the found alignments.

In some embodiments, the identifying transcripts include identifying known isoforms and novel isoforms. Upon identifying a novel isoform, the directed acyclic data structure may be updated to include new nodes or edges to be used in representing the novel isoform.

The method may include identifying expression levels of the transcripts.

In certain aspects, the invention provides a computer system for analyzing transcriptomes that includes a non-transitory memory coupled to a processor, the system having stored therein a directed acyclic data structure comprising nodes representing RNA sequences and edges connecting pairs of nodes. The system is operable to obtain a plurality of sequence reads from a transcriptome, find alignments— each with an alignment score that meets a predetermined criteria—between the plurality of sequence reads and the directed acyclic data structure, and identify transcripts in the transcriptome based on paths through the directed acyclic data structure that include the alignments. In some embodiments, finding the alignments includes finding preliminary alignments, determining an observed frequency of isoforms based on the preliminary alignments, comparing the observed frequency of isoforms to an expected frequency of isoforms, and making new alignments with a penalty factor to minimize a difference between the observed frequency and the expected frequency. In certain embodiments, the predetermined criteria comprises the highest-scoring alignment. In some embodiments, the directed acyclic data structure represents substantially all known exons and introns for at least one chromosome. Optionally, the directed acyclic data structure is created and stored prior to the finding the alignments. The system may be operable to identify known isoforms and novel isoforms in the transcriptome. Preferably the system is operable to update the directed acyclic data structure to include new edges used in representing the novel isoforms. In certain embodiments, the system is operable to identify expression levels of the transcripts. The alignments may be found by comparing each sequence read to at least a majority of the possible paths through the directed acyclic data structure. In some embodiments, the system is operable to assemble the plurality of sequence reads into a contig based on the found alignments.

BRIEF DESCRIPTION OF THE DRAWINGS

FIG. 2 shows the actual matrices that correspond to the comparison.

FIG. 4 presents three alternative histories involving sequences.

DETAILED DESCRIPTION

Figure 1:
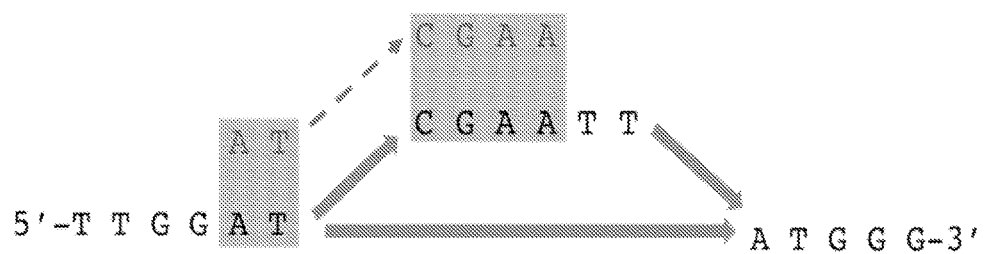
FIG. 1 shows a pictorial representation of the read being compared to the DAG.

It is understood that genes do not in general code for single, specific proteins. Instead, different subsets of a given gene's exons are transcribed in different proportions at different times. The different proteins created by these different transcripts are called isoforms, and by extension the different transcripts themselves are also called isoforms. As discussed above, contemporary bioinformatics has provided at least partially annotated transcriptomes, potentially useful as references. For example, the Gencode project has catalogued not only genes but exons (along with other regions) in the human genome.

Systems and methods described herein are used to efficiently exploit the information in those annotated transcriptomes. Indeed, the invention includes the insight that comparison of RNA-Seq reads to an annotated transcriptome is ideally suited to analytical approaches in which sequence data is stored as a DAG-based data structure.

Embodiments of the invention involve creating a directed acyclic data structure with the data from an annotated transcriptome. In such a data structure, features (e.g., exons and introns) from the annotated transcriptome are represented as nodes, which are connected by edges. An isoform from the real-world transcriptome is thus represented by a corresponding path through the DAG-based data structure.

Aspects of the invention relate to creation of a DAG that includes features such as introns and exons from one or more known references. A DAG is understood in the art to refer to data that can be presented as a graph as well as to a graph that presents that data. The invention provides methods for storing a DAG as data that can be read by a computer system for informatic processing or for presentation as a graph. A DAG can be saved in any suitable format including, for example, a list of nodes and edges, a matrix or a table representing a matrix, an array of arrays or similar variable structure representing a matrix, in a language built with syntax for graphs, in a general markup language purposed for a graph, or others.

In some embodiments, a DAG is stored as a list of nodes and edges. One way to do this is to create a text file that includes all nodes, with an ID assigned to each node, and all edges, each with the node ID of starting and ending node. Thus, for example, were a DAG to be created for two sentences, "See Jane run," and "Run, Jane run,", a case-insensitive text file could be created. Any suitable format could be used. For example, the text file could include comma-separated values. Naming this DAG "Jane" for future reference, in this format, the DAG "Jane" may read as follows: 1 see, 2 run, 3 jane, 4 run, 1-3, 2-3, 3-4. One of skill in the art will appreciate that this structure is easily applicable to the introns and exons represented in FIGS. 4 and 5, and the accompanying discussion below.

In certain embodiments, a DAG is stored as a table representing a matrix (or an array of arrays or similar variable structure representing a matrix) in which the (i,j) entry in the matrix denotes whether node i and node j are connected. For the DAG to be acyclic simply requires that all non-zero entries be above the diagonal (assuming indices are correctly ordered). In a binary case, a 0 entry represents that no edge is exists from node i to node j, and a 1 entry represents an edge from i to j. One of skill in the art will appreciate that a matrix structure allows values other than 0 to 1 to be associated with an edge. For example, any entry may be a numerical value indicating a weight, or a number of times used, reflecting some natural quality of observed data in the world. A matrix can be written to a text file as a table or a linear series of rows (e.g., row 1 first, followed by a separator, etc.), thus providing a simple serialization structure.

One useful way to serialize a matrix DAG would be to use comma-separated values for the entries, after defining the nodes. Using this format, the DAG "Jane" would include the same node definitions as for above, followed by matrix entries. This format could read as:

1 see, 2 run, 3 jane, 4 run

,,1,\,,1,\,,,1\,,, where zero (0) entries are simply omitted and '\' is a newline character.

Embodiments of the invention include storing a DAG in a language built with syntax for graphs. For example, The DOT Language provided with the graph visualization software package known as Graphviz provides a data structure that can be used to store a DAG with auxiliary information and that can be converted into graphic file formats using a number of tools available from the Graphviz web site. Graphviz is open source graph visualization software. Graph visualization is a way of representing structural information as diagrams of abstract graphs and networks. It has important applications in networking, bioinformatics, software engineering, database and web design, machine learning, and in visual interfaces for other technical domains. The Graphviz programs take descriptions of graphs in a simple text language, and make diagrams in useful formats, such as images and SVG for web pages; PDF or Postscript for inclusion in other documents; or display in an interactive graph browser.

In related embodiments, a DAG is stored in a general markup language purposed for a graph, or others. Following the descriptions of a linear text file, or a comma-separated matrix, above, one of skill in the art will recognize that a language such as XML can be used (extended) to create labels (markup) defining nodes and their headers or IDs, edges, weights, etc. However a DAG is structured and stored, embodiments of the invention involve using nodes to represent features such as exons and introns. This provides a useful tool for analyzing RNA-Seq reads and discovering, identifying, and representing isoforms.

If nodes represent features or fragments of features, then isoforms can be represented by paths through those fragments. An exon's being "skipped" is represented by an edge connecting some previous exon to some later one. Presented herein are techniques for constructing a DAG to represent alternative splicing or isoforms of genes. Alternative splicing is discussed in Lee and Wang, 2005, Bioinformatics analysis of alternative splicing, Brief Bioinf 6(1):23-33; Heber, et al., 2002, Splicing graphs and EST assembly problems, Bioinformatics 18Suppl:s181-188; Leipzig, et al., 2004, The alternative splicing gallery (ASG): Bridging the gap between genome and transcriptome, Nucl Ac Res 23(13):3977-2983; and LeGault and Dewey, 2013, Inference of alternative splicing from RNA-Seq data with probabilistic splice graphs, Bioinformatics 29(18):2300-2310, the contents of each of which are incorporated by reference. Additional discussion may be found in Florea, et al., 2005, Gene and alternative splicing annotation with AIR, Genome Research 15:54-66; Kim, et al., 2005, ECgene: Genome-based EST clustering and gene modeling for alternative splicing, Genome Research 15:566-576; and Xing, et al., 2006, An expectation-maximization algorithm for probabilistic reconstructions of full-length isoforms from splice graphs, Nucleic Acids Research, 34, 3150-3160, the contents of each of which are incorporated by reference.

1. Construction of the "Maximal DAG."

Aspects of the invention relate to creation of a maximal DAG that includes all or substantially all known features of a reference. Unlike methods such as those described by Leipzig, et al. (2004), creating a maximal DAG includes connecting every possible pair from the set of introns and exons even without experimental evidence (e.g., Leipzig's splicing graph represented transcripts supported by direct evidence). A maximal DAG data structure according to the invention includes every possible edge and has applications in transcriptomics including, for example, identifying isoforms.

A maximal DAG may be created by obtaining information about features such as introns and exons from some source and representing those features as nodes. Feature information may be obtained from any suitable source including, for example, genomic sequences (e.g., by recognizing transcription initiation sites, splice sites, and open reading frames to infer the locations of exons and introns); newly generated data (e.g., by sequencing the genome of an organism); from a database or annotated transcriptome; or a combination thereof. Any suitable database can be used, such as, for example, Gencode, Ensembl, RefSeq, STACK, or others. The information on intron and exon features is used to create nodes representing those exons, introns, and other features. For example, Gencode provides enough information to associate with these nodes such information as a sequence for the node, the positions it occupies in a reference sequence (and therefore its length), and so on. Important elements of the maximal DAG include nodes and edges, however, any other information such as sequence or length may be included. In some embodiments, nodes or edges are associated with scores or other extrinsic values. For example, edges may be given weights or scores (discussed in greater detail below).

Creation of a maximal DAG provides a tool that can be used to identify an isoform. Since each possible isoform will be included, by definition, in the maximal DAG, when incoming data (e.g., reads from RNA-Seq) is compared to the DAG, even if those data are from an isoform for which there is no a priori evidence, a match will be found. Making the maximal DAG includes representing each of a plurality of features from a genome as a node and creating, for each pair of the plurality of features, an edge connecting the two members of the pair by their proximal ends.

An important step of the method involves creating an edge, for each pair of the features, connecting the two members of that pair by their proximal ends. Thus if the features are P, Q, R, S, and T, then the pairs are PQ, PR, PS, PT, QR, QS, QT, RS, RT, and ST. Remembering that P, Q, R, S, and T represent genomic features, the proximal ends of the members of a pair would be the 3' end of the upstream feature and the 5' end of the downstream feature, where 5' is—by definition—upstream of 3'.

The features may be obtained from Gencode or some such source. The steps are performed using a computer system that includes a processor coupled to a non-transitory memory. The nodes and edges are stored as a directed acyclic data structure in the memory. Preferably, each of substantially all of the exons from the genome is represented as node. One interesting feature of a maximal DAG is that introns may be represented as nodes (e.g., co-equally with exons). Including the introns as if they were exons allows for unexpected or novel isoforms and alternative splicings to be discovered. Also, in contrast to prior art alternative splicing studies, including the introns may be important from the point of view of transcriptomics as the discovery or quantification of pre-mRNA may be included in objectives of the study.

Using the maximal DAG, a sequence from a transcript can thus be aligned to a path through the DAG that includes a subset of the features connected by a subset of the edges. The path, since it matches a transcript read from experimental data, is thus understood to represent an isoform.

One aspect of the maximal DAG is that every pair of nodes is connected, in their genomic order, by an edge that extends from the node representing the "earlier" or "left-side" exon to the "later" or "right-side" exon. The biological interpretation of such a move is to conjecture the existence of, or at least to facilitate the discovery of, isoforms representing every combination of exons that respects the order in which those exons appear in the genome. There are both inductive reasons and biochemical reasons to respect the order in which exons appear in the genome.

For example, reports suggest that exons in multi-exon pre-mRNAs are always maintained in order. See, e.g., Black, 2005, A simple answer for a splicing conundrum, PNAS 102:4927-8. Without being bound by any particular mechanism, it may be theorized that splicing machinery recognizes the start and end of introns, as well as branch-point adenines or other conserved sequences proximal to splice junctions. The splicing machinery, or splicesome, moves along the pre-mRNA from 5' to 3' removing the introns and splicing the exons. Thus it appears that there is phenomenological as well as literature support for connecting all exons in the 5' to 3' order in which they appear along the genomic DNA strand. See also Shao et al., 2006, Bioinformatic analysis of exon repetition, exon scrambling and trans-splicing in humans, Bioinformatics 22: 692-698. For certain assumptions, methods of the invention follow the assumption that human pre-mRNAs are spliced into linear molecules that retain the exon order defined by the genomic sequence.

Additionally, where it is desirable to include instances of exon scrambling (see, e.g., Carrington et al., 1985, Polypeptide ligation occurs during post-translational modification of concanavalin A, Nature 313:64-67) in a directed acyclic data structure, the assumption that exons are spliced in their original order can be maintained substantially by including duplicate exons as a "fiction" (or, in the alternative, the assumption can be abandoned).

Accordingly where, for example, a genome includes the following exons in the following order: ABCDEFGHI using dashes as edges and letters as nodes, the complete set of edges can be represented by:

A-C; A-D; A-E; A-F; A-G; A-H; A-I; B-C; B-D; B-E; B-F; B-G; B-H; B-I; C-D; C-E; C-F; C-G; C-H; C-I; D-E; D-F; D-G; D-H; D-I; E-F; E-G; E-H; E-I; F-G; F-H; F-I; G-H; G-I.

If this proves adequate to discover all isoforms but one, and that one isoform is—to give an example: ADEHG Then, the acyclic data structure can be "spiked" with an artificial, or fictitious, G—call it G'. Then that isoform can be represented by A-D-E-H-G' and the structure need not include any edge from H to G. However, it may be found that exon scrambling can be ignored and genomic exon order maintained by all included edges.

A DAG of the invention may first be prepared by using input data from an annotated transcriptome. As such, ab initio, the DAG will include all known isoforms. Preferably, the DAG will include all possible edges that maintain genomic exon order and will thus then include nodes and edges that represent both known and novel isoforms. It is noted that the paths that exist in a maximal DAG may be represented by an N×N matrix P for N introns and exons wherein all $P_{ij}$, $i>j=1$ and all $P_{ij}$, $i \leq 0$.

It is also noted that when new data is aligned to the maximal DAG (e.g., RNA-Seq reads), those data may include exons that had not been identified in the annotated reference. As the exon is novel in this example, so is the isoform. Use of a DAG as the reference is ideally suited to this circumstance as aligning a novel isoform to an existing DAG can also guide the creation of a new node in the DAG to represent the novel exon (i.e., represent a newly discovered exon by adding a row and a column to P, creating an N+1×N+1 matrix Q). Thus, where an identified isoform is novel, aligning the transcript sequence can involve creating a new node in the directed acyclic data structure. A new node can also be created for splice variants, e.g., where one exon differs from another by a single codon.

Preferably, the maximal DAG is initially built—all or partly—prior to and independent of analyzing RNA-Seq reads. Thus, the method may include creating the edge for each pair of the plurality of features prior to aligning the transcript. For reasons related to the nature of directed acyclic data structures, the reference represented in the data structure can be arbitrarily large—e.g., hundreds or thousands of exons, introns, or both.

2. Alignment.

Aspects of the invention relate to aligning sequence reads to a directed acyclic data structure that, in some embodiments, substantially comprehensively represents an annotated reference. Using alignment algorithms of the invention, reads can be rapidly mapped despite the large numbers associated with RNA-Seq results and substantially comprehensive references. As in other situations, DAGs are ideal objects against which to align. Performing alignments against DAGs constructed out of annotated transcriptomes is much more effective than using the annotated transcriptomes later in one's workflow.

Numerous benefits obtain by using a DAG as a reference. For example, aligning against a DAG is more accurate than aligning against one reference and then attempting to adjust one's results in light of an annotated transcriptome. This is primarily because the latter approach enforces an unnatural asymmetry between the sequence used in the initial alignment and the other sequences represented in the transcriptome. Moreover, given that it is desired to align against an object that represents all the relevant physical possibilities, accomplishing this with a DAG is much more computationally efficient than attempting to align against a linear sequence for each physical possibility (the number of such possibilities will generally be exponential in the number of junctions). To obtain these accuracies and efficiencies, the invention provides systems and methods that can be used to align a read against objects representing all or most physical possibilities.

Embodiments of the invention include aligning one or more reads against a reference data structure. That alignment can include a DAG-based alignment that finds the edges and nodes of the data structure that best represent the read. That alignment can also include instances of aligning a read to an exon from a node of the DAG in a pairwise fashion.

Pairwise alignment generally involves placing one sequence along another sequence, gaps may be introduced along each sequence, scoring how well the two sequences match, and preferably repeating for various position along the reference. The best-scoring match is deemed to be the alignment and represents an inference about the historical relationship between the sequences. In an alignment, a base in the read alongside a non-matching base in the reference indicates that a substitution mutation has occurred at that point. Similarly, where one sequence includes a gap alongside a base in the other sequence, an insertion or deletion mutation (an "indel") may be inferred to have occurred.

In some embodiments, scoring an alignment of a pair of nucleic acid sequences involves setting values for the probabilities of substitutions and indels. When individual bases are aligned, a match or mismatch contributes to the alignment score by a substitution probability, which could be, for example, 1 for a match and −0.33 for a mismatch. An indel deducts from an alignment score by a gap penalty, which could be, for example, −1. Gap penalties and substitution probabilities can be based on empirical knowledge or a priori assumptions about how sequences evolve. Their values affects the resulting alignment. Particularly, the relationship between the gap penalties and substitution probabilities influences whether substitutions or indels will be favored in the resulting alignment.

Stated formally, an alignment represents an inferred relationship between two sequences, x and y. For example, in some embodiments, an alignment A of sequences x and y maps x and y respectively to another two strings x' and y' that may contain spaces such that: (i) $|x'|=|y'|$; (ii) removing spaces from x' and y' should get back x and y, respectively; and (iii) for any i, x'[i] and y'[i] cannot be both spaces.

A gap is a maximal substring of contiguous spaces in either x' or y'. An alignment A can include the following three kinds of regions: (i) matched pair (e.g., x'[i]=y'[i]; (ii) mismatched pair, (e.g., x'[i]≠y'[i] and both are not spaces); or (iii) gap (e.g., either x'[i . . . j] or y'[i . . . j] is a gap). In certain embodiments, only a matched pair has a high positive score a. In some embodiments, a mismatched pair generally has a negative score b and a gap of length r also has a negative score g+rs where g, s<0. For DNA, one common scoring scheme (e.g. used by BLAST) makes score a=1, score b=−3, g=−5 and s=−2. The score of the alignment A is the sum of the scores for all matched pairs, mismatched pairs and gaps. The alignment score of x and y can be defined as the maximum score among all possible alignments of x and y.

In some embodiments, any pair has a score a defined by a 4×4 matrix B of substitution probabilities. For example, $B(i,i)=1$ and $0<B(i,j)i<>j<1$ is one possible scoring system. For instance, where a transition is thought to be more biologically probable than a transversion, matrix B could include $B(C,T)=0.7$ and $B(A,T)=0.3$, or any other set of values desired or determined by methods known in the art.

Alignment according to some embodiments of the invention includes pairwise alignment. A pairwise alignment, generally, involves—for sequence Q (query) having m characters and a reference genome T (target) of n characters—finding and evaluating possible local alignments between Q and T. For any $1 \leq i \leq n$ and $1 \leq j \leq m$, the largest possible alignment score of T[h ... i] and Q[k ... j], where $h \leq i$ and $k \leq j$, is computed (i.e. the best alignment score of any substring of T ending at position i and any substring of Q ending at position j). This can include examining all substrings with cm characters, where c is a constant depending on a similarity model, and aligning each substring separately with Q. Each alignment is scored, and the alignment with the preferred score is accepted as the alignment. One of skill in the art will appreciate that there are exact and approximate algorithms for sequence alignment. Exact algorithms will find the highest scoring alignment, but can be computationally expensive. Two well-known exact algorithms are Needleman-Wunsch (J Mol Biol, 48(3):443-453, 1970) and Smith-Waterman (J Mol Biol, 147(1):195-197, 1981; Adv. in Math. 20(3), 367-387, 1976). A further improvement to Smith-Waterman by Gotoh (J Mol Biol, 162(3), 705-708, 1982) reduces the calculation time from O(m2n) to O(mn) where m and n are the sequence sizes being compared and is more amendable to parallel processing. In the field of bioinformatics, it is Gotoh's modified algorithm that is often referred to as the Smith-Waterman algorithm. Smith-Waterman approaches are being used to align larger sequence sets against larger reference sequences as parallel computing resources become more widely and cheaply available. See, e.g., Amazon's cloud computing resources. All of the journal articles referenced herein are incorporated by reference in their entireties.

The Smith-Waterman (SW) algorithm aligns linear sequences by rewarding overlap between bases in the sequences, and penalizing gaps between the sequences. Smith-Waterman also differs from Needleman-Wunsch, in that SW does not require the shorter sequence to span the string of letters describing the longer sequence. That is, SW does not assume that one sequence is a read of the entirety of the other sequence. Furthermore, because SW is not obligated to find an alignment that stretches across the entire length of the strings, a local alignment can begin and end anywhere within the two sequences.

In some embodiments, pairwise alignment proceeds according to dot-matrix methods, dynamic programming methods, or word methods. Dynamic programming methods generally implement the Smith-Waterman (SW) algorithm or the Needleman-Wunsch (NW) algorithm. Alignment according to the NW algorithm generally scores aligned characters according to a similarity matrix S(a,b) (e.g., such as the aforementioned matrix B) with a linear gap penalty d. Matrix S(a,b) generally supplies substitution probabilities. The SW algorithm is similar to the NW algorithm, but any negative scoring matrix cells are set to zero. The SW and NW algorithms, and implementations thereof, are described in more detail in U.S. Pat. No. 5,701,256 and U.S. Pub. 2009/0119313, both herein incorporated by reference in their entirety. It may be preferable or desirable to implement the a modified version of the SW alignment algorithm when aligning RNA-Seq reads to a directed acyclic annotated reference.

When aligning two strings of length n and m, the SW algorithm may be expressed for an n×m matrix H, representing the two strings, in terms of equation (1):

$$H\_k0 = H\_0l = 0 \text{ (for } 0 \leq k \leq n \text{ and } 0 \leq l \leq m) \tag{1}$$

$$H\_ij = \max\{H\_(i-1,j-1) + s(a\_i, b\_j), H\_(i-1,j) - W\_\text{in},$$
$$H\_(i,j-1) - W\_\text{del}, 0\} \text{ (for } 1 \leq i \leq n \text{ and } 1 \leq j \leq m)$$

In the equations above, s(ai,bj) represents either a match bonus (when ai=bj) or a mismatch penalty (when ai≠bj), and insertions and deletions are given the penalties Win and Wdel, respectively. In most instance, the resulting matrix has many elements that are zero. This representation makes it easier to backtrace from high-to-low, right-to-left in the matrix, thus identifying the alignment.

Once the matrix has been fully populated with scores, the SW algorithm performs a backtrack to determine the alignment. Starting with the maximum value in the matrix, the algorithm will backtrack based on which of the three values (Hi−1,j−1, Hi−1,j, or Hi,j−1) was used to compute the final maximum value for each cell. The backtracking stops when a zero is reached. The optimal-scoring alignment may contain greater than the minimum possible number of insertions and deletions, while containing far fewer than the maximum possible number of substitutions.

When applied as SW or SW-Gotoh, the techniques use a dynamic programming algorithm to perform local sequence alignment of the two strings, S and A, of sizes m and n, respectively. This dynamic programming technique employs tables or matrices to preserve match scores and avoid re-computation for successive cells. Each element of the string can be indexed with respect to a letter of the sequence, that is, if S is the string ATCGAA, S[1]=A.

Instead of representing the optimum alignment as Hi,j (above), the optimum alignment can be represented as B[j,k] in equation (2) below:

$$B[j,k] = \max(p[j,k], i[j,k], d[j,k], 0) \text{ (for } 0 < j \leq m, \ 0 < k \leq n) \tag{2}$$

The arguments of the maximum function, B[j,k], are outlined in equations (3)-(5) below, wherein MISMATCH_PENALTY, MATCH_BONUS, INSERTION_PENALTY, DELETION_PENALTY, and OPENING_PENALTY are all constants, and all negative except for MATCH_BONUS. The match argument, p[j,k], is given by equation (3), below:

$$p[j,k] = \max(p[j-1,k-1], i[j-1,k-1], d[j-1,k-1]) + \text{MISMATCH\_PENALTY, if } S[j] \neq A[k] = \max(p[j-1,k-1], i[j-1,k-1], d[j-1,k-1]) + \text{MATCH\_BONUS, if } S[j] = A[k] \tag{3}$$

the insertion argument i[j,k], is given by equation (4), below:

$$i[j,k] = \max(p[j-1,k] + \text{OPENING\_PENALTY}, i[j-1,k], d[j-1,k] + \text{OPENING\_PENALTY}) + \text{INSERTION\_PENALTY} \tag{4}$$

and the deletion argument d[j,k], is given by equation (5), below:

$$d[j,k] = \max(p[j,k-1] + \text{OPENING\_PENALTY}, i[j,k-1] + \text{OPENING\_PENALTY}, d[j,k-1]) + \text{DELETION\_PENALTY} \tag{5}$$

For all three arguments, the [0,0] element is set to zero to assure that the backtrack goes to completion, i.e., p[0,0]=i[0,0]=d[0,0]=0.

The scoring parameters are somewhat arbitrary, and can be adjusted to achieve the behavior of the computations. One example of the scoring parameter settings (Huang, Chapter 3: Bio-Sequence Comparison and Alignment, ser. Curr Top Comp Mol Biol. Cambridge, Mass.: The MIT Press, 2002) for DNA would be:

MATCH_BONUS: 10
MISMATCH_PENALTY: −20
INSERTION_PENALTY: −40
OPENING_PENALTY: −10
DELETION_PENALTY: −5

The relationship between the gap penalties (INSERTION_PENALTY, OPENING_PENALTY) above help limit the number of gap openings, i.e., favor grouping gaps together, by setting the gap insertion penalty higher than the gap opening cost. Of course, alternative relationships between MISMATCH_PENALTY, MATCH_BONUS, INSERTION_PENALTY, OPENING_PENALTY and DELETION_PENALTY are possible.

In some embodiments, the methods and systems of the invention incorporate multi-dimensional alignment algorithms such as a modified SW alignment algorithm. Multi-dimensional algorithms of the invention provide for a "lookback" type analysis of sequence information (as in Smith-Waterman), wherein the look back is conducted through a multi-dimensional space that includes multiple pathways and multiple nodes. The multi-dimensional algorithm can be used to align RNA-Seq reads against the DAG-type reference. That alignment algorithm identifies the maximum value for Ci,j by identifying the maximum score with respect to each sequence contained at a position on the DAG (e.g., the reference sequence construct). In fact, by looking "backwards" at the preceding positions, it is possible to identify the optimum alignment across a plurality of possible paths.

The algorithm of the invention is carried out on a read (a.k.a. "string") and a directed acyclic graph (DAG), discussed above. For the purpose of defining the algorithm, let S be the string being aligned, and let D be the directed acyclic graph to which S is being aligned. The elements of the string, S, are bracketed with indices beginning at 1. Thus, if S is the string ATCGAA, S[1]=A, S[4]=G, etc.

In certain embodiments, for the DAG, each letter of the sequence of a node will be represented as a separate element, d. A predecessor of d is defined as:

(i) If d is not the first letter of the sequence of its node, the letter preceding d in its node is its (only) predecessor;

(ii) If d is the first letter of the sequence of its node, the last letter of the sequence of any node (e.g., all exons upstream in the genome) that is a parent of d's node is a predecessor of d.

The set of all predecessors is, in turn, represented as P[d].

In order to find the "best" alignment, the algorithm seeks the value of M[j,d], the score of the optimal alignment of the first j elements of S with the portion of the DAG preceding (and including) d. This step is similar to finding Hi,j in equation 1 above. Specifically, determining M[j,d] involves finding the maximum of a, i, e, and 0, as defined below:

$$M[d] = \max\{a, i, e, 0\} \quad (6)$$

where $$e = \max\{M[j, p^*] + \text{DELETE\_PENALTY}\} \text{ for } p^* \text{ in } P[d]$$

$$i = M[j-1, d] + \text{INSERT\_PENALTY}$$

$$a = \max\{M[j-1, p^*] + \text{MATCH\_SCORE}\} \text{ for } p^* \text{ in } P[d], \text{ if } S[j] = d;$$

$$\max\{M[j-1, p^*] + \text{MISMATCH\_PENALTY}\} \text{ for } p^* \text{ in } P[d], \text{ if } S[j] \neq d$$

As described above, e is the highest of the alignments of the first j characters of S with the portions of the DAG up to, but not including, d, plus an additional DELETE_PENALTY. Accordingly, if d is not the first letter of the sequence of the node, then there is only one predecessor, p, and the alignment score of the first j characters of S with the DAG (up-to-and-including p) is equivalent to M[j,p]+DELETE_PENALTY. In the instance where d is the first letter of the sequence of its node, there can be multiple possible predecessors, and because the DELETE_PENALTY is constant, maximizing [M[j, p*]+DELETE_PENALTY] is the same as choosing the predecessor with the highest alignment score with the first j characters of S.

In equation (6), i is the alignment of the first j−1 characters of the string S with the DAG up-to-and-including d, plus an INSERT_PENALTY, which is similar to the definition of the insertion argument in SW (see equation 1).

Additionally, a is the highest of the alignments of the first j characters of S with the portions of the DAG up to, but not including d, plus either a MATCH_SCORE (if the jth character of S is the same as the character d) or a MISMATCH_PENALTY (if the jth character of S is not the same as the character d). As with e, this means that if d is not the first letter of the sequence of its node, then there is only one predecessor, i.e., p. That means a is the alignment score of the first j−1 characters of S with the DAG (up-to-and-including p), i.e., M[j−1,p], with either a MISMATCH_PENALTY or MATCH_SCORE added, depending upon whether d and the jth character of S match. In the instance where d is the first letter of the sequence of its node, there can be multiple possible predecessors. In this case, maximizing {M[j, p*]+MISMATCH_PENALTY or MATCH_SCORE} is the same as choosing the predecessor with the highest alignment score with the first j−1 characters of S (i.e., the highest of the candidate M[j−1,p*] arguments) and adding either a MISMATCH_PENALTY or a MATCH_SCORE depending on whether d and the jth character of S match.

Again, as in the SW algorithm, the penalties, e.g., DELETE_PENALTY, INSERT_PENALTY, MATCH_SCORE and MISMATCH_PENALTY, can be adjusted to encourage alignment with fewer gaps, etc.

As described in the equations above, the algorithm finds the optimal (i.e., maximum) value for each read by calculating not only the insertion, deletion, and match scores for that element, but looking backward (against the direction of the DAG) to any prior nodes on the DAG to find a maximum score. Thus, the algorithm is able to traverse the different paths through the DAG, which contain the known mutations. Because the graphs are directed, the backtracks, which move against the direction of the graph, follow the preferred isoform toward the origin of the graph, and the optimal alignment score identifies the most likely alignment within a high degree of certainty.

Implementation of the disclosed algorithm is exemplified in FIG. 1, where a sequence "ATCGAA" is aligned against a DAG that represents a reference sequence TTGGATATGGG (SEQ ID NO: 1) and a known insertion event TTGGATCGAATTATGGG (SEQ ID NO: 2), where the insertion is underlined.

FIG. 1 shows a pictorial representation of the read being compared to the DAG. The top area of FIG. 1 presents a sequence read "ATCGAA" as well as a reference sequence TTGGATATGGG (SEQ ID NO: 1) and a known insertion event TTGGATCGAATTATGGG (SEQ ID NO: 2), where the insertion is underlined. The middle of FIG. 1 shows a relationship among the read, SEQ ID NO:1, and SEQ ID NO: 2, keeping each sequence linear to aid in visualizing the relationship. The bottom area of FIG. 1 shows the alignment constructed using a DAG. In the depicted DAG, SEQ ID NOS. 1 and 2 can both be read by reading from the 5' end of the DAG to the 3' end of the DAG, albeit along different paths. The sequence read is shown as aligning to the upper path as depicted.

Figure 2:
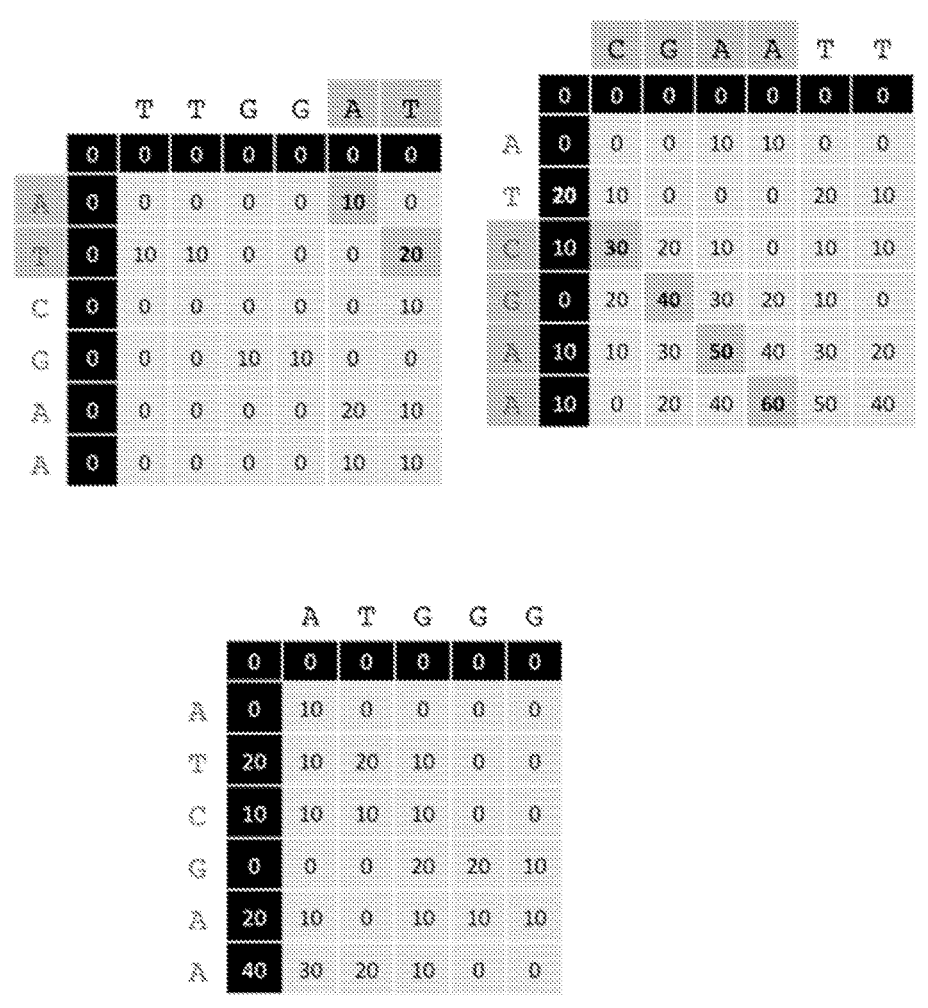

FIG. 2 shows the actual matrices that correspond to the comparison. Like the Smith-Waterman technique, the illustrated algorithm of the invention identifies the highest score and performs a backtrack to identify the proper location of the read. FIGS. 1 and 2 also highlight that the invention produces an actual match for the string against the construct. In the instances where the sequence reads include variants that were not included in the DAG, the aligned sequence will be reported out with a gap, insertion, etc.

Aligning RNA-Seq reads to a DAG of an annotated reference allows one to discover isoforms in a transcriptome. Additionally, the possibility that different forms of alternative splicing have occurred (e.g., the possibility that one codon has been skipped in one of the relevant exons) can be anticipated "for free."

Exons can be automatically separated into two nodes, one corresponding to the first codon and one corresponding to the rest of the exon; this allows both kinds of splicing to be represented in the DAG even if they have not yet been observed. Anticipating these situations can be useful, given that one codon's worth of differences to an alignment will often not punish a candidate alignment enough to induce us to look for alternatives. (The largest such penalty would be that for three insertions or three deletions, and often the penalty will be smaller due to chance.)

Representing the transcriptome as a DAG permits a natural interpretation of an isoform as a path through the DAG. As is common when one represents a physical item in a mathematical structure, the benefits are numerous. For example, systems and methods of the invention allow sequences to be visualized in an intuitive way. Sequences can be compared, for example, by showing two paths through a DAG.

Additionally, methods of the invention are conducive to exploiting graph theorems and algorithms. The analysis of paths through DAGs is a vibrant research area in modern mathematics and computer science. The ability to exploit this research to improve the study of the transcriptome is therefore valuable. For example, if edges were to be given weights corresponding to the probabilities of junctions' being spanned by reads, then the total weight of a path could carry information about the a priori possibilities that different isoforms are realized. Maximizing (or minimizing) weights of paths through DAGs is known, and a shortest-path algorithm could be used to find those shortest paths quickly.

Figure 3:
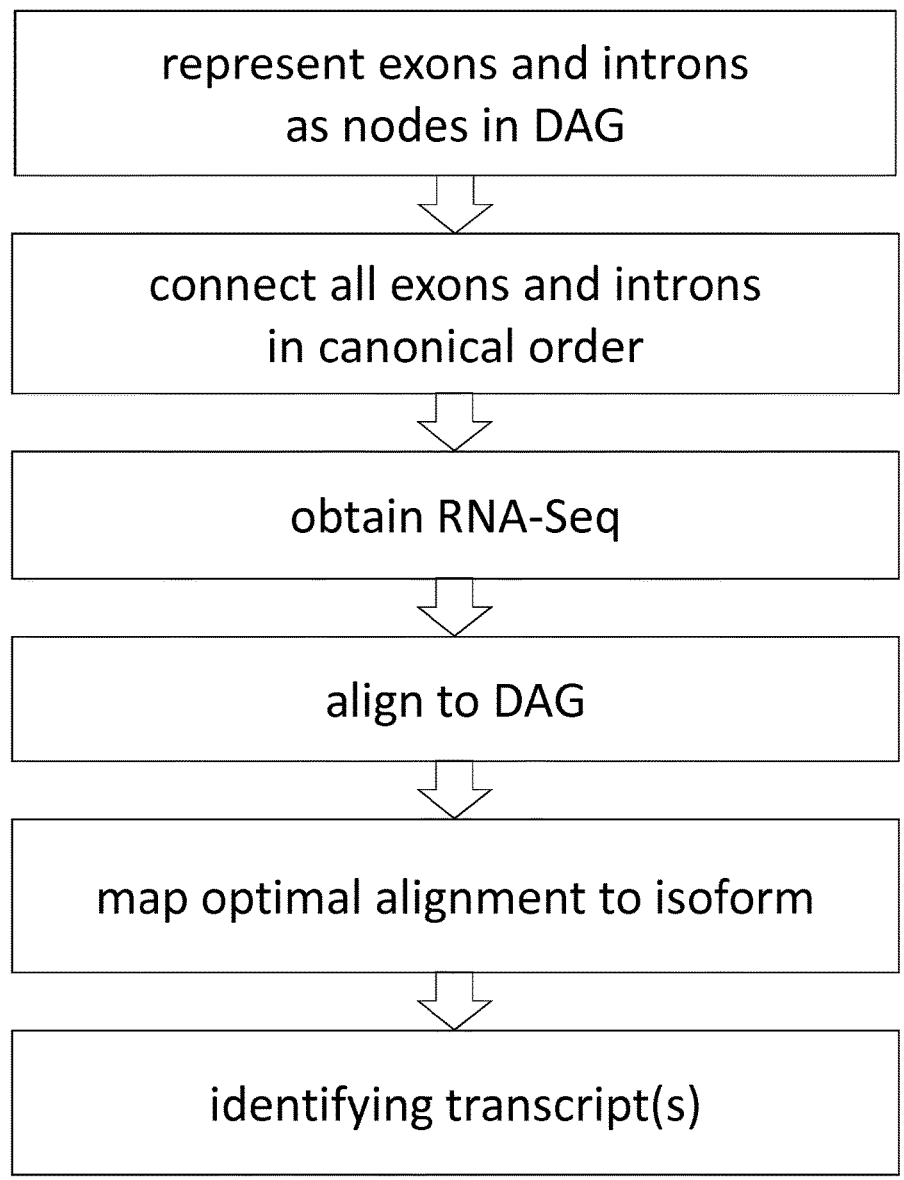
FIG. 3 provides a diagram of methods of the invention.

FIG. 3 provides a diagram of methods of the invention. A DAG is built with exons, introns, or both connected in canonical order. In some embodiments, the maximal DAG is built that includes substantially all exons and introns and an edge for every pair. RNA-Seq reads are obtained. For each read, a best alignment is found (having an alignment score that meets a predetermined criteria) between the plurality of sequence reads and a directed acyclic data structure comprising nodes representing RNA sequences and edges connecting each pair of nodes. Transcripts in the transcriptome are identified based on paths through the directed acyclic data structure that include the alignments.

Methods of the invention are suited for analysis of reads obtained by RNA-Seq. The predetermined criteria for selecting the best alignment may be, for example, the highest-scoring alignment. Preferably, the directed acyclic data structure represents substantially all known features for at least one chromosome. The directed acyclic data structure may be created and stored prior to the finding the alignments. In some embodiments, the alignments are found by comparing each sequence read to at least a majority of the possible paths through the directed acyclic data structure. The method may include assembling the plurality of sequence reads into a contig based on the found alignments. Additional discussion may be found in Lee, et al., 2002, Multiple sequence alignment using partial order graphs, Bioinformatics 18(3):452-464 and Yap, et al., 2003, A graph-theoretic approach to comparing and integrating genetic, physical and sequence-based maps, Genetics 165: 2235-2247, the contents of which are incorporated by reference.

3. Sensitivity to Varieties of Alternative Splicing.

Current techniques make it difficult or impossible to distinguish between several kinds of situations when a read spans the junction of exons. One such situation is where mutations have occurred. Another such situation arises when, even in the absence of mutations, a read may appear not to match on either side of a junction because a form of alternative splicing has occurred in which part of a codon has been included or skipped. Also, sequencing errors present another such situation.

Consider, as an example, the following sequence:

(SEQ ID NO: 3)
AUGCAUUUCCGUGGAUAGCGAUGCAUACUCACGAUG AUGAAA

AUGCAUCAGAAAUAG where plain text regions (first 18 characters and last 15 characters) represent exons, the first underlined portion represents an intron, and the second underlined portion is a region that, due to alternative splicing, might or not be included in the second exon. Thus the mature RNA might take either of two forms:

(SEQ ID NO: 4)
AUGCAUUUCCGUGGAUAGAUGAAAAUGCAUCAGAAAUAG (SEQ ID NO: 5)
AUGCAUUUCCGUGGAUAGAUGCAUCAGAAAUAG

Now suppose that the following read is obtained: TGGA-TAGATGAA (SEQ ID NO: 6). Such a read could have several causal histories that differ in important ways.

FIG. 4 presents three alternative histories involving these sequences. In the first situation depicted across the top third of FIG. 4, the read is taken from SEQ ID NO: 4, and no mutation or sequencing error has occurred. In the second situation, the read is taken from SEQ ID NO: 5, and a sequencing error has occurred. In the third situation, the read is taken from transcript SEQ ID NO: 5, and the read accurately reflects a mutation.

If a linear reference sequence consists only of the plain text region (e.g., only SEQ ID NO: 5), it is very likely that the alignment score will be so high—boosted by many matches and having suffered only one mismatch penalty— that the algorithm in use will not flag the alignment as possibly erroneous. Rather than examine some other file or database for splicing information, it will simply posit a mutation or single sequencing error.

Figure 5:
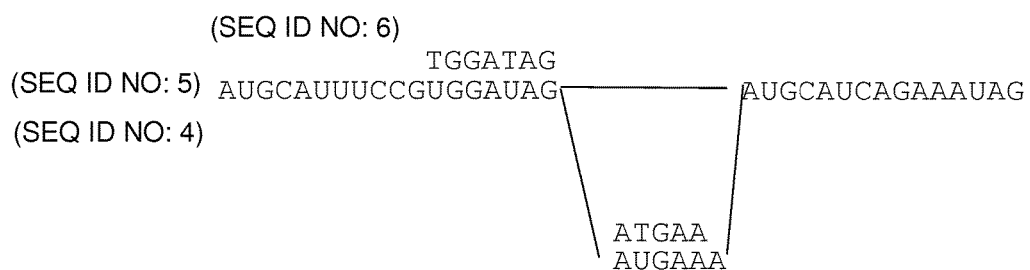
FIG. 5 depicts an alignment according to the invention.

Aligning against a DAG reference does better. FIG. 5 depicts an alignment of SEQ ID NO: 3 against a DAG reference (appearing now in FIG. 5 as SEQ ID NO: 4 since the intron is gone). Here the accurate alignment is immediately recovered, as it will have the highest score of any possible alignment to this DAG. Due to the nature of a DAG, FIG. 5 also depicts:

```
                                           (SEQ ID NO: 5)
        AUGCAUUUCCGUGGAUAGAUGCAUCAGAAAUAG
```

This is a very general phenomenon and will occur often, given how often small parts of exons are subject to inclusion or exclusion by alternative splicing. A system involving linear references will usually fail to detect mischaracterizations when these situations arise, and the only way to prevent these mistakes is to align against so many linear references as to make the process prohibitively expensive (in both time and money).

4. Incorporating a Priori Exon- and Isoform-Count Distributions.

The invention includes methods and systems for transcriptome analysis in which a DAG is used for a reference. The DAG need not be a maximal DAG. The invention exploits situations in which there is an a priori data for the relative frequency of isoform counts. Isoform distributions for transcripts may be inferred to correlate to distributions of protein isoforms. Questions about the distribution of exon- and isoform-counts for a given gene, and the way in which these distributions are sensitive to other facts about a sequence (e.g., whether it is a coding or non-coding sequence), have been studied thoroughly, if incompletely. Isoform frequencies may be obtained from the literature or by performing an analysis. For example, isoform frequencies may be inferred from paired-end read RNA-Seq reads, as described in Section 6, 'Using paired-end data: inferring isoform frequency', below. In some embodiments, insert sizes from paired-end read data are used to infer isoform frequencies, as described in Section 7, 'Using insert sizes more effectively to infer isoform probabilities', below. In certain embodiments, isoform frequencies are obtained from a source such as a database or the literature.

Figure 6:
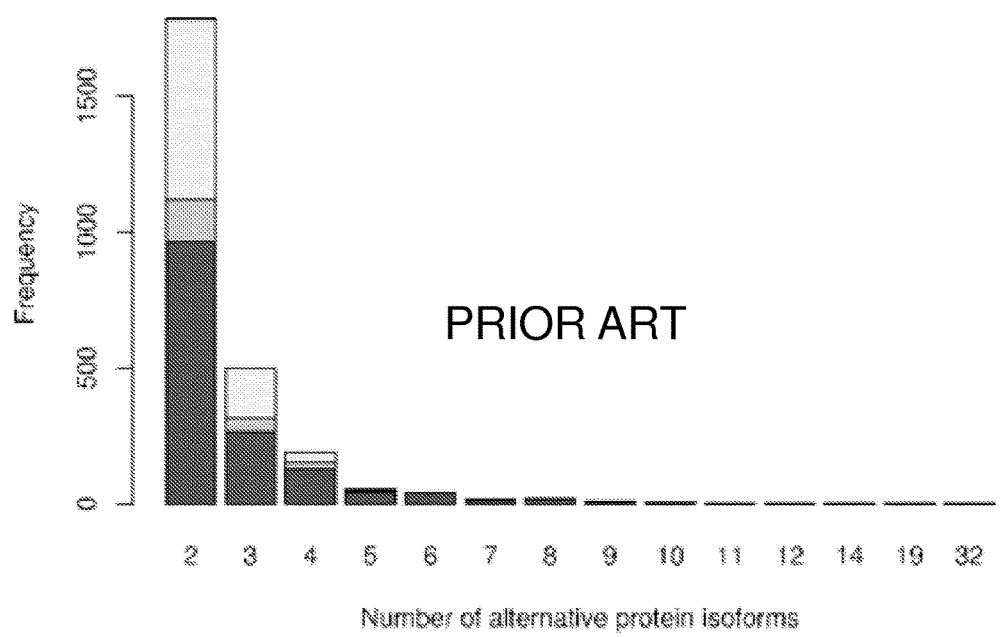
FIG. 6 shows an isoform frequency distribution.

FIG. 6 represents protein isoform distributions obtained by a study using SwissProt amino acid sequence, and is a reproduction of the FIG. 3 from Nakao, et al., 2005, Large-scale analysis of human alternative protein isoforms: pattern classification and correlation with subcellular localization signals, Nucl Ac Res 33(8):2355-2363. Additionally, Chang, et al., have used programming methods to deduce quantitative distributions of various alternative splicing forms. Chang, et al., 2005, The application of alternative splicing graphs in quantitative analysis of alternative splicing form from EST database, Int J. Comp. Appl. Tech 22(1):14.

The information presented by FIG. 6 represents an isoform count distribution that can be used to aid in mapping reads to a DAG. Similarly, exon count distribution information may be obtained.

For example, there is a demonstrated distribution of number of exons per transcript. See, e.g., Harrow, et al., 2012, GENCODE: The reference human genome annotation for The ENCODE Project, Genome Res 22:1760-1774. Transcripts at protein-coding loci demonstrate a peak at four exons per transcript, while lncRNAs show a distinct peak at two exons (see FIG. 2 of Harrow, et al., 2012). The exon count distribution from Harrow, et al., or the isoform distribution from Nakao, et al., could be interpreted probabilistically, with the y-axis giving relative instead of absolute frequency. Such information may be used to inform judgments about the likelihood that candidate alignments correspond to actual nucleotide sequences. Prior art techniques rely primarily on the scores of the alignments. The invention provides ways of including a priori knowledge of isoform number.

For example, for a large set of reads, 75% may unambiguously map to regions in a set of eight isoforms {I1, I2, . . . , I8}, while the other 25% of which could be interpreted as mapping either to I5 or to some other combination of exons corresponding to a further isoform I9. In this situation, various kinds of facts are relevant to the decision how to align that last 25% of reads. Such relevant facts include (i) the scores of the alignments to I5 and to I9; (ii) any further knowledge about the regulatory mechanisms; and (iii) whether it is more likely a priori for there to be eight or nine isoforms.

The invention incorporates isoform distribution information when mapping reads to a DAG reference. Isoform frequency distribution information may be used in several different ways. A first exemplary method of including a priori isoform number in mapping reads includes: (1) constructing a DAG for the relevant region of the genome (the edges of this DAG can be weighted or unweighted) and (2) associating—with each edge of the DAG—a value that indicates the edge's usage. Set the usage "off" if the number of reads aligned in a way that spans that edge is smaller than some variable U. This variable intuitively reflects whether the edge has been "used." One way to estimate it might be by setting it equal to (the number of reads in the sample)*(the quotient of a reasonable estimate of the length of an exon and the average read length)*(0.005).

Further, the method includes (3) associating with the relevant region of the genome a variable corresponding to a usage threshold T, perhaps setting T equal to the expected value of the number of edges used in the graph plus the standard deviation of the number of edges used in the graph. These numbers could be calculated using standard techniques for estimating the number of edges in a DAG that has the numbers of nodes and maximal paths corresponding to empirical exons frequencies, isoform frequencies, or both that would be expected for the gene in question. The empirical frequencies could be obtained, for example, from Harrow, et al., 2012 for exon count distribution or from Nakao, et al., 2005, for isoform distribution.

The method includes (4) modifying the scoring scheme used in Smith-Waterman or other algorithms, punishing the traversal of an unused edge by some penalty if the total number of "used" edges (i.e., edges for which the Boolean usage value is "on" or "true") N exceeds T. This penalty may be made to increase as N increases. A reasonable formula for the penalty might be max(0,(N−T)*(the insertion penalty)*2). The zero term appears to avoid negative penalties—i.e., to avoid bonuses for using new edges—but such bonuses might be appropriate in some contexts, in which case there is no need to take the maximum of zero and the latter expression's value.

To avoid unwelcome path dependencies in the form of the alignments' being sensitive to the order in which the reads are processed, one might repeat the alignments several times and compare the results. This does not affect the asymptotic running time of the algorithm.

An alternative exemplary method of including a priori isoform number in mapping reads includes:

(i) align each read against the DAG;

(ii) compare an observed number of isoforms to an expected number of isoforms (e.g., obtained from an a priori probability distribution of the number of isoforms given background information about the gene); and (iii) if the difference between the observed number and the expected number exceeds some threshold, re-align the reads that were assigned to the rarest candidate isoforms. In the re-alignment, any alignment to a rare candidate isoform is penalized with a weight that depends on the magnitude of the difference. The penalty may be max(0,(N−T)*(the insertion penalty)*2), where N is a total number of "used" edges (i.e., edges for which the Boolean usage value is "on" or "true") and T is a usage threshold. In some embodiments, T is an expected value of the number of edges used in the graph plus the standard deviation of the number of edges used in the graph.

By application of methods of using a priori probability distribution of the number of isoforms, the reads being mapped to the DAG will be pushed to result in a distribution that approaches the a priori distribution.

5. Using Paired-End Reads

Other aspects of the invention relate to transcriptomics involving RNA-Seq data that includes paired-reads. Systems and methods of the invention provide for improved alignments using paired-end reads.

In certain particular embodiments, paired-end reads are used to constrain alignments, thereby greatly improving computational cost of an RNA-Seq project.

Much sequencing data is paired-end data. There exist ways in which features of such data ought to manifest themselves in alignments: the distance between the locations to which paired-end mates are assigned in alignment ought approximately to correspond to the insert size given by the sequencing run. In general, information given by insert sizes is related to the information that alignment algorithms attempt to uncover.

Several methods are known in the art for producing paired nucleic acid reads. Typically, the methods involve some form of selectively fragmenting a nucleic acid sample, resulting in sequences of a known size distribution. The ends of the fragmented samples are typically protected with a functional group or by self-cyclizing, whereupon the remaining nucleic acid sample material is removed. The ends are then amplified and sequenced, resulting in a population of nucleic acid reads that are known to have originated some distance from each other.

Mate pair sample preparation kits are commercially available, for example from Nextera Illumina (San Diego, Calif.). To prepare paired nucleic acids for sequencing on such a platform, a nucleic acid sample is fragmented into segments between 2 and 5 kb in length. The fragment ends are then biotinylated to facilitate later recovery using affinity column separation. The biotinylated ends are joined to create a circular DNA segment. At this point, non-circularized nucleic acids from the sample are digested and subsequently removed. The remaining circularized DNA is then re-fragmented to yield fragments suitable for clustering and sequencing. The original ends, which are biotinylated, can be removed from the remaining fragments of the circularized DNA with an affinity column or streptavidin coated beads. The recovered ends are then end repaired, poly-A tailed, and sequencing adapters are added prior to amplification and sequencing.

One way in which insert size information can be combined with a DAG is to use insert sizes as a constraint on alignment. There are possible gains both in speed and in accuracy from using this method. The method is more accurate than aligning the paired-end mates separately because it keeps one from discarding important information relevant to the alignment. It is noted that aligning two paired-end mates independently amounts, approximately, to choosing two locations among the L possible locations in the genome (if the genome has length L). Thus the aligning involves choosing among roughly $L^2$ possibilities. However, the first alignment is used to strongly constrain the other alignment to some region of constant size k around the first alignment, then there are only roughly kL possibilities—on the order of L, not $L^2$. This will be much faster.

This constraint can be enacted by a method that includes aligning one of a set of paired-end mates. If the alignment is sufficiently good (as measured by alignment score), then all exons within a certain range (e.g., three standard deviations) of the expected value of the distance between the mates are considered. The other mate is then aligned to the considered exons, and not the whole genome.

The invention includes methods of modifying a DAG using paired-end data.

The invention provides additional exploits of the relationship between the insert size and the correct alignments. One can view the current paradigm as treating the insert size as a constraint on a given alignment or pair of alignments. This is an incomplete description of the situation. It may be more accurate to view insert sizes as a constraint on the combination of the alignments and the transcript.

Methods of the invention involve using insert sizes as a quality control not only on the alignments but also on the transcript. If each of two paired-end mates has a high-scoring alignment in the transcript DAG (which may or may not be a "maximal DAG" as described above), and if this pair of alignments corresponds to a grossly implausible insert size, it will often be more reasonable to adjust beliefs about the transcript (e.g., by adding edges to the graph) than to adjust our beliefs about the correctness of each of the alignments.

This can be implemented by—whenever two paired-end mates align to a DAG—calculate the insert size or sizes implied by that alignment. (More than one size might be involved because the read might be consistent with several features.) If the quotient of the smallest such insert size and the expected value of the insert size is greater than some constant (perhaps 2), examine the DAG to find a pair of unconnected nodes which, if connected, would entail the existence of an isoform for which the quotient of the implied insert size for that isoform and the expected value of the insert size is between 0.5 and 1.5. If such a pair of nodes exists, connect them with an edge. If several such pairs exist, choose the one that yields the ratio closest to 1 and connect it.

In certain aspects, the invention provides a method of analyzing a transcriptome that involves obtaining at least one pair of paired-end reads from a cDNA fragment, finding an alignment with an optimal score between a first read of the pair and a node in a directed acyclic data structure (the data structure has nodes representing RNA sequences such as exons or transcripts and edges connecting each pair of nodes), identifying candidate paths that include the node connected to a downstream node by a path having a length substantially similar to a length of the cDNA fragment, and aligning the paired-end rends to the candidate paths to determine an optimal-scoring alignment. The method is suited for a number of paired-end reads from cDNA fragments (e.g., cDNA fragments representing a single transcriptome). The node and the downstream node may represent a pair of exons from which the pair of paired-end reads were obtained. The method may include identifying an isoform based on the determined optimal-scoring alignment. In some embodiments, the identified isoform is a novel isoform. The directed acyclic data structure may be updated to represent the novel isoform (e.g., by adding at least one new node or edge).

In some embodiments, the length of the cDNA fragment is the insert length of the pair of paired-end reads.

The method may include excluding any paths that are not candidate paths from any alignment calculations involving the pair of paired-end reads.

Other aspects of the invention provide for expression analysis through, e.g., systems and methods useful for inferring isoform frequency.

6. Using Paired-End Data: Inferring Isoform Frequency.

A powerful technique arises not from using paired-end structure to align properly, but from using alignment to infer isoform frequency with the intermediate step of inferring insert sizes from alignment. If the frequency with which pairs of exons appear in a sample is known (see, e.g., Harrow, 2012, Genome Research 22:1760), those frequencies can be used to construct the frequencies with which isoforms appear in a sample. Moreover, different pairs of exons will usually be separated by different distances. Thus, the distances observed between paired-end mates can be used (slightly indirectly) to keep track of exon frequencies.

An illustrative example is as follows. For each pair of paired end mates, the pair may first optionally be aligned to the DAG reference. The distances between a reference point (e.g., the left-most position) on each pair member is noted and tracked. This can be obtained from the alignment to the DAG, although it is noted that methods of inferring isoform frequency may not require aligning the pairs to the DAG.

One suitable method for noting and tracking the distances between the reference point for each aligned pair is through the use of a hash table. In the distance hash, keys may be all distances between 1 and 1000 and the values of each key are initialized to zero. Incrementing can then be done by looking up the value of the key corresponding to the distance and incrementing that value. Note that this sort of manipulation of a hash table can be done extremely fast—indeed, in constant time. Additionally it is noted that hash tables are well-supported by existing bioinformatics packages such as BioPerl. Each pair of exons is then associated with the sum of the values corresponding to the distances nearest the true distance between the exons. (That is: add up all the "hits" observed for distances close to the distance between those exons. The quotient of that number and the total number of pairs will be very close to the frequency with which that pair of exons occurs, relative to all pairs of exons, in the sample.)

From this data, isoform frequency can be determined algebraically. The preferred form of equation may depend on the structure of relevant isoforms, but a general technique obtains, as follows:

Suppose that there are three isoforms, one of which contains exons A, B, and C, another of which contains exons A, B, and D, and the third of which contains exons B, C, and D. The frequencies of the exon pairs—where [AB] is the frequency of the exon pair AB among all of the aligned reads—is obtained from the aligned reads (i.e., each time exon i is connected to exon j in an alignment, the corresponding frequency is incremented by one).

Then, if the frequencies of the three isoforms are (in order) [A]=f, [B]=g, and [C]=h, the frequencies of the exon-pairs should be as follows:

$$[AB]=f+g$$

$$[BC]=f+h$$

$$[BD]=g+h$$

As the left-hand values are known from the alignment, the isoform frequencies can be solved. In general, methods of the invention include writing equations relating exon-pair-frequencies to isoform-frequencies and use the former to obtain the latter. One of skill in the art will recognize algebraic methods for solving the depicted equations. To give an illustrative example, it is noted that algebraic manipulation of the above yields:

$$f=[AB]-g,$$

and:

$$h=[BD]-g$$

Thus:

$$[BC]=f+[BD]-g$$

and:

$$[BC]=[AB]-g+[BD]-g$$

Rearrangement provides:

$$[BC]/2([AB]+[BD])=g$$

Since [BC], [AB], and [BD] are all known from the alignment, g is thus calculated. Solving for f and h is then trivial.

In some circumstances, there may appear to be a "degree of freedom" problem in that the number of variables to be solved is not less than the number of input variables. Any suitable technique for addressing this apparent problem could be employed and may depend on the particular circumstance. Suitable techniques may be found to include normalizing the variables; solving for more than one set of isoform frequencies and choosing one after-the-fact; obtaining at least on input value extrinsically (e.g., from the biological sample), or providing input information (e.g., from the literature or an assumption).

It is important to note a graphical interpretation of the key step: suppose a graph is produced having distances on the x-axis and frequencies on the y-axis. Exon-pairs will then appear as peaks on that graph, and frequently some of those peaks will be readily interpretable as isoform-frequencies also.

In certain aspects, the invention provides a method of inferring isoform frequency in a transcriptome by a plurality of pairs of paired-end reads from cDNA and optionally aligning those reads to a reference data structure. The data structure includes a plurality of exons from a genome each represented as a node. Pairs of nodes, or exons, are connected at their proximal ends by an edge. Distances between the aligned pairs of the paired-end reads and the frequencies of the distances between the aligned pairs are determined. A set of isoform paths and isoform frequencies are determined such that representing the isoform paths through the structure at the isoform frequencies results in pairs of exons being included in the isoform paths at the frequencies of the distances the aligned pairs. Each path of the determined set of isoform paths may represent a transcript isoform present in the organism. The distances between the aligned pairs may be path lengths from an upstream end of a first aligned member of each pair to a downstream end of a second aligned member of that pair.

In some embodiments, the cDNA represents substantially an entire transcriptome of an organism. In certain embodiments, determining the set of isoform path includes discovering a novel isoform path. The reference data structure may be updated to include the novel isoform path.

Determining the set of isoform paths can be performed algebraically, e.g., by solving a set of linear equations. In some embodiments, the one of the isoform frequencies is obtained from biological data prior to solving the set of linear equations (e.g., so remaining variables in the linear equations can be determined). Additionally or alternatively, the frequencies of the distances between the aligned pairs may be normalized prior to determining a set of isoform paths and isoform frequencies.

7. Using Insert Sizes More Effectively to Infer Isoform Probabilities.

Suppose that two exons E1 and E2 occur in different isoforms and that they are separated by distances L1 and L2 in those two isoforms. It will occasionally happen that there are obtained paired-end reads for which one mate maps to E1 and the other to E2. The choice of which isoform to attribute this pair to can then be reduced to the question whether to infer that L1 or L2—or one of those distances shifted by an appropriate amount given the mates' offsets from the edge of the exon—is the true distance between the reads.

Translating the isoform-assignment question to a question about insert sizes is valuable because there is often background information available about the distribution of insert sizes in a paired-end sequencing run. Given that there will usually be no other reason to believe that the read would more likely to have been taken from one isoform or the other, a simple Bayesian calculation can assign the read probabilistically to the two isoforms according to the ratio of the probabilities of insert sizes L1 and L2 in the distribution.

This is a marked improvement on current techniques, which generally view reads as carrying equal evidential weight for the two isoforms in this case. Incorporating the insert size in the way described is therefore a way of not ignoring relevant evidence.

Thus, isoforms in these ambiguous cases may be counted as follows:

(1) Calculate a probability distribution of insert sizes. (Denote by P(s) the probability of a read's having insert size s.) Note that this needs to be calculated only once and that this could be done in a preprocessing step.

(2) If each of two paired-end mates maps inside an exon:
(2a) Make a list of all the isoforms that include those exons.
(2b) Associate with each isoform the insert size that would be implied by the read's having derived from that isoform.
(2c) Calculate P(s) for each of the insert sizes calculated in (2b).
(2d) Associate with each isoform the relevant value of P(s) divided by the sum of all the P(s) values calculated in (2c).

It is noted that techniques described herein will improve read counts of isoforms in a way that does not affect one's ability to use "downstream" tools—that is, tools that take read counts as inputs and give other useful outputs.

8. Systems of the Invention

Figure 7:
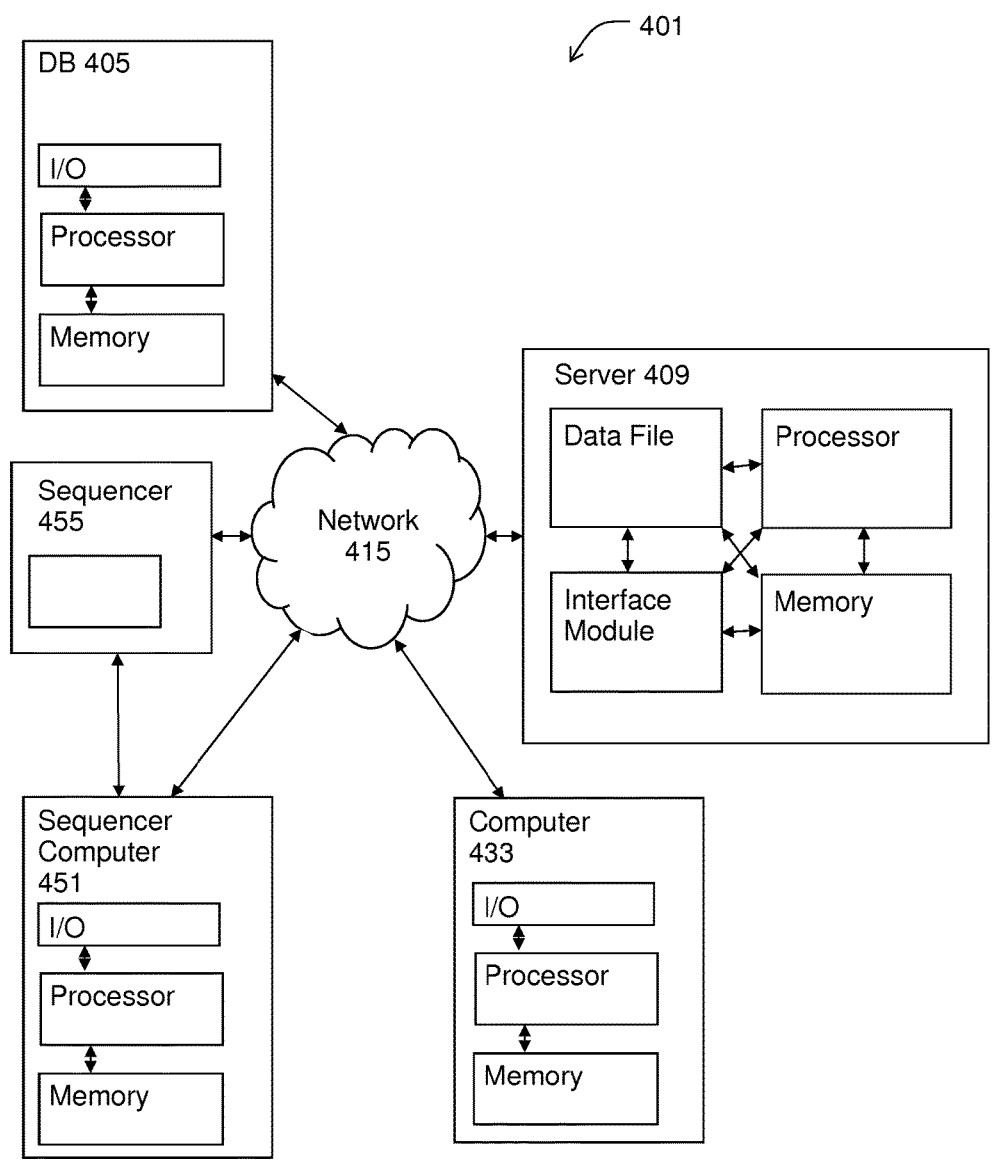
FIG. 7 illustrates a system for implementing methods of the invention.

FIG. 7 illustrates a computer system 401 useful for implementing methodologies described herein. A system of the invention may include any one or any number of the components shown in FIG. 7. Generally, a system 401 may include a computer 433 and a server computer 409 capable of communication with one another over network 415. Additionally, data may optionally be obtained from a database 405 (e.g., local or remote). In some embodiments, systems include an instrument 455 for obtaining sequencing data, which may be coupled to a sequencer computer 451 for initial processing of sequence reads.

In some embodiments, methods are performed by parallel processing and server 409 includes a plurality of processors with a parallel architecture, i.e., a distributed network of processors and storage capable of comparing a plurality of sequences (e.g., RNA-Seq reads) to a reference sequence construct (e.g., a DAG). The system comprises a plurality of processors that simultaneously execute a plurality of comparisons between a plurality of reads and the reference sequence construct. While other hybrid configurations are possible, the main memory in a parallel computer is typically either shared between all processing elements in a single address space, or distributed, i.e., each processing element has its own local address space. (Distributed memory refers to the fact that the memory is logically distributed, but often implies that it is physically distributed as well.) Distributed shared memory and memory virtualization combine the two approaches, where the processing element has its own local memory and access to the memory on non-local processors. Accesses to local memory are typically faster than accesses to non-local memory.

Computer architectures in which each element of main memory can be accessed with equal latency and bandwidth are known as Uniform Memory Access (UMA) systems. Typically, that can be achieved only by a shared memory system, in which the memory is not physically distributed. A system that does not have this property is known as a Non-Uniform Memory Access (NUMA) architecture. Distributed memory systems have non-uniform memory access.

Processor—processor and processor—memory communication can be implemented in hardware in several ways, including via shared (either multiported or multiplexed) memory, a crossbar switch, a shared bus or an interconnect network of a myriad of topologies including star, ring, tree, hypercube, fat hypercube (a hypercube with more than one processor at a node), or n-dimensional mesh.

Parallel computers based on interconnected networks must incorporate routing to enable the passing of messages between nodes that are not directly connected. The medium used for communication between the processors is likely to be hierarchical in large multiprocessor machines. Such resources are commercially available for purchase for dedicated use, or these resources can be accessed via "the cloud," e.g., Amazon Cloud Computing.

A computer generally includes a processor coupled to a memory and an input-output (I/O) mechanism via a bus. Memory can include RAM or ROM and preferably includes at least one tangible, non-transitory medium storing instructions executable to cause the system to perform functions described herein. As one skilled in the art would recognize as necessary or best-suited for performance of the methods of the invention, systems of the invention include one or more processors (e.g., a central processing unit (CPU), a graphics processing unit (GPU), etc.), computer-readable storage devices (e.g., main memory, static memory, etc.), or combinations thereof which communicate with each other via a bus.

A processor may be any suitable processor known in the art, such as the processor sold under the trademark XEON E7 by Intel (Santa Clara, Calif.) or the processor sold under the trademark OPTERON 6200 by AMD (Sunnyvale, Calif.).

Input/output devices according to the invention may include a video display unit (e.g., a liquid crystal display (LCD) or a cathode ray tube (CRT) monitor), an alphanumeric input device (e.g., a keyboard), a cursor control device (e.g., a mouse or trackpad), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

The invention claimed is:

1. A system for analyzing a transcriptome, the system comprising:
   a processor coupled to a non-transitory memory, wherein the system is operable to:
   represent each of a plurality of features from a genome as a node, wherein the features comprise exons and introns;
   create, for each pair of the plurality of features, an edge connecting the two members of the pair by their proximal ends, thereby creating a directed acyclic graph (DAG) representing substantially all possible splice variants of the plurality of features such that each node is directly connected to every other node by at least one edge;
   store the nodes and the edges as the DAG in the memory;
   align a transcript sequence from a transcriptome of an organism to a path comprising a subset of the exons and introns connected by a subset of the edges, wherein the aligning comprises calculating match scores between the transcript sequence and the nodes in the DAG, and looking backwards to predecessor nodes in the DAG to transform the transcript sequence into a back-trace with an optimal score, wherein the back-trace with the optimal score is the path; and
   identify the path as at least a portion of an isoform from the transcriptome of the organism.

2. The system of claim 1, further operable to obtain, from an annotated transcriptome database, information about the plurality of features to be represented.

3. The system of claim 1, wherein the transcript sequence includes a novel exon, where novel exon means one that is in the transcriptome and not in the annotated transcriptome database, and the system is further operable to create a new node in the DAG to represent the novel exon, thereby transforming the DAG to reflect discovery of the novel exon.

4. The system of claim 1, further operable to create the edge for each pair of the plurality of features prior to aligning the transcript sequence.

5. The system of claim 1, wherein the system is further operable to represent each of substantially all of the exons from the genome as nodes.

6. The system of claim 1, wherein the plurality of features comprises all of the exons of a gene.

7. The system of claim 1, wherein a one of the plurality of features and a second one of the plurality of features represent alternative versions of an exon differing by one codon.

8. The system of claim 1, wherein a one of the plurality of features exists within a second one of the plurality of features on the genome.

9. The system of claim 1, wherein the plurality of features includes at least 100 exons.

10. A system for analyzing a transcriptome, the system comprising:
    a processor coupled to a non-transitory memory, wherein the system is operable to:
    obtain from an annotated transcriptome database a plurality of exons and introns from a genome;
    transform each of the plurality of exons and introns from the annotated transcriptome database into a node;
    create, for each pair of the plurality of exons and introns, an edge connecting the two members of the pair by their proximal ends, thereby transforming the plurality of exons and introns from the annotated transcriptome database into a directed acyclic graph (DAG) representing substantially all possible splice variants of the plurality of exons and introns wherein each and every pair of nodes is directly connected by at least one edge with no intervening nodes between that pair of nodes along that edge, wherein the DAG contains at least one pair of nodes connected by an edge that is not supported by evidence from the annotated transcriptome database;
    store the nodes and the edges as the DAG in the memory;
    obtain a plurality of sequence reads generated by sequencing a transcriptome of an organism;
    align the plurality of sequence reads from the transcriptome to a path comprising a subset of the exons and introns connected by a subset of the edges, wherein the aligning comprises calculating match scores between the plurality of sequence reads and the nodes in the DAG, and looking backwards to predecessor nodes in the DAG to transform the plurality of sequence reads into a back-trace with an optimal score, wherein the back-trace with the optimal score is the path; and
    identify the path as at least a portion of an isoform from the transcriptome of the organism.

11. The system of claim 10, wherein the edge for each pair of the plurality of exons and introns is created by the processor prior to aligning the transcript.

12. The system of claim 11, further operable to represent each of substantially all of the exons from the genome as nodes.

13. The system of claim 10, wherein the plurality of sequence reads further includes a novel exon, where novel exon means one that is found in the transcriptome and not in the annotated transcriptome database, and the system is further operable to create a new node in the DAG to represent the novel exon, thereby transforming the DAG to reflect discovery of the novel exon.

14. The system of claim 10, wherein the plurality of exons and introns comprises all of the exons of a gene.

15. The system of claim 10, wherein the plurality of sequence reads further includes a novel exon, where novel exon means one that is found in the transcriptome and not in the annotated transcriptome database, and the system is further operable to create a new node in the DAG to represent the novel exon, thereby transforming the DAG to reflect discovery of the novel exon.

16. The system of claim 10, wherein a one of the plurality of exons and introns and a second one of the plurality of exons and introns represent alternative versions of an exon differing by one codon.

17. The system of claim 10, wherein a one of the plurality of exons and introns exists within a second one of the plurality of features on the genome.

18. The system of claim 10, wherein the plurality of exons and introns includes at least 100 exons.

19. The system of claim 10, wherein each node is connected to every other node in their canonical order.

20. The system of claim 10, wherein the path comprises a skipped codon.

* * * * *

SEQUENCE LISTING

```
<160> NUMBER OF SEQ ID NOS: 6

<210> SEQ ID NO 1
<211> LENGTH: 11
<212> TYPE: DNA
<213> ORGANISM: Homo sapiens

<400> SEQUENCE: 1
ttggatatgg g                                                          11

<210> SEQ ID NO 2
<211> LENGTH: 17
<212> TYPE: DNA
<213> ORGANISM: Homo sapiens

<400> SEQUENCE: 2
ttggatcgaa ttatggg                                                    17

<210> SEQ ID NO 3
<211> LENGTH: 57
<212> TYPE: RNA
<213> ORGANISM: Homo sapiens

<400> SEQUENCE: 3
augcauuucc guggauagcg augcauacuc acgaugauga aaaugcauca gaaauag        57

<210> SEQ ID NO 4
<211> LENGTH: 39
<212> TYPE: RNA
<213> ORGANISM: Homo sapiens

<400> SEQUENCE: 4
augcauuucc guggauagau gaaaaugcau cagaaauag                            39

<210> SEQ ID NO 5
<211> LENGTH: 33
<212> TYPE: RNA
<213> ORGANISM: Homo sapiens

<400> SEQUENCE: 5
augcauuucc guggauagau gcaucagaaa uag                                  33

<210> SEQ ID NO 6
<211> LENGTH: 12
```

```
<212> TYPE: DNA
<213> ORGANISM: Homo sapiens

<400> SEQUENCE: 6
tggatagatg aa                                                         12
```